(12) United States Patent
Toreki et al.

(10) Patent No.: US 8,343,523 B2
(45) Date of Patent: *Jan. 1, 2013

(54) DISINFECTANT WITH DURABLE ACTIVITY BASED ON ALCOHOL-SOLUBLE QUATERNARY AMMONIUM POLYMERS AND COPOLYMERS

(75) Inventors: William Toreki, Gainesville, FL (US); Gerald Olderman, Bedford, MA (US); Rustom S. Kanga, Marietta, GA (US)

(73) Assignee: Quick-Med Technologies, Inc., Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/350,784

(22) Filed: Jan. 8, 2009

(65) Prior Publication Data

US 2009/0117164 A1 May 7, 2009

Related U.S. Application Data

(63) Continuation-in-part of application No. 12/064,487, filed as application No. PCT/US2006/032954 on Aug. 22, 2006, now Pat. No. 8,088,400.

(60) Provisional application No. 61/019,798, filed on Jan. 8, 2008, provisional application No. 60/806,196, filed on Jun. 29, 2006, provisional application No. 60/710,128, filed on Aug. 22, 2005.

(51) Int. Cl.
*A01N 33/02* (2006.01)
*A01N 25/00* (2006.01)
*A01P 1/00* (2006.01)

(52) U.S. Cl. .................. 424/405; 424/78.08; 424/78.17

(58) Field of Classification Search .................. 424/405
See application file for complete search history.

(56) References Cited

U.S. PATENT DOCUMENTS

| | | | | |
|---|---|---|---|---|
| 4,789,720 A | * | 12/1988 | Teffenhart | 528/76 |
| 4,846,165 A | * | 7/1989 | Hare et al. | 228/156 |
| 5,084,096 A | | 1/1992 | Stovicek | |
| 5,597,561 A | | 1/1997 | Kross | |
| 5,776,430 A | | 7/1998 | Osborne et al. | |
| 5,817,325 A | | 10/1998 | Sawan et al. | |
| 5,849,311 A | | 12/1998 | Sawan et al. | |
| 5,869,073 A | | 2/1999 | Sawan et al. | |
| 5,869,600 A | | 2/1999 | Causton et al. | |
| 5,906,808 A | | 5/1999 | Osborne et al. | |
| 5,916,568 A | | 6/1999 | Smyth et al. | |
| 6,015,816 A | * | 1/2000 | Kostyniak et al. | 514/299 |
| 6,030,632 A | | 2/2000 | Sawan et al. | |
| 6,126,931 A | | 10/2000 | Sawan et al. | |
| 6,177,523 B1 | * | 1/2001 | Reich et al. | 525/459 |
| 6,180,584 B1 | | 1/2001 | Sawan et al. | |
| 6,194,530 B1 | * | 2/2001 | Klesse et al. | 526/312 |
| 6,217,887 B1 | | 4/2001 | Beerse et al. | |
| 6,264,936 B1 | | 7/2001 | Sawan et al. | |
| 6,369,289 B1 | | 4/2002 | Orr, III | |
| 6,441,045 B1 | | 8/2002 | Birnbaum et al. | |
| 6,482,402 B1 | * | 11/2002 | Kurtz et al. | 424/78.17 |
| 6,627,207 B1 | | 9/2003 | Petersen et al. | |
| 7,459,167 B1 | * | 12/2008 | Sengupta et al. | 424/405 |
| 2002/0177828 A1 | * | 11/2002 | Batich et al. | 604/367 |
| 2004/0123963 A1 | * | 7/2004 | Chen et al. | 162/134 |
| 2006/0051385 A1 | | 3/2006 | Scholz | |
| 2009/0042870 A1 | | 2/2009 | Fellows et al. | |

FOREIGN PATENT DOCUMENTS

| | | |
|---|---|---|
| JP | 2006-213708 A | 8/2006 |
| WO | 2007024973 A1 | 3/2007 |

OTHER PUBLICATIONS

Silver, S., "Bacterila silver resistance: molecular biology and uses and misuses of silver compounds." FEMS Microbiology Reviews, 2003; 27:341-353.

* cited by examiner

*Primary Examiner* — Richard Schnizer
*Assistant Examiner* — Audrea Buckley
(74) *Attorney, Agent, or Firm* — Gerry J. Elman; Elman Technology Law, P.C.

(57) ABSTRACT

An alcohol- or glycol-soluble, water-insoluble, disinfectant composition and a method of using the same for disinfecting and for providing a prolonged antimicrobial property to a variety of surfaces, including skin. The composition comprises at least one alcohol or glycol and an antimicrobial polymer that is capable of imparting an antimicrobial property to a surface without the use of a metal or a metal-containing compound. The composition is applied to a surface and allowed to evaporate leaving a coating of antimicrobial polymer. Alternatively, the composition is incorporated into or within the substrate.

19 Claims, No Drawings

DISINFECTANT WITH DURABLE ACTIVITY BASED ON ALCOHOL-SOLUBLE QUATERNARY AMMONIUM POLYMERS AND COPOLYMERS

CROSS-REFERENCE TO RELATED APPLICATIONS

This application claims priority to U.S. Provisional Patent Application 61/019,798 filed Jan. 8, 2008. This application is also a continuation in part of our co-pending U.S. patent application Ser. No. 12/064,487 filed Feb. 22, 2008 which is a national phase entry of PCT/US2006/32954 (WO2007/024973) filed Aug. 22, 2006 which claims priority to Provisional Patent Application 60/806,196 filed on Jun. 29, 2006 and Provisional Patent Application 60/710,128 filed Aug. 22, 2005. The entire disclosures of each of the aforementioned references are incorporated herein by reference.

TECHNICAL FIELD

This invention relates to disinfectants compositions for coating and adhesive applications. The disinfectants provide sustained antimicrobial activity for prolonged periods following their application to the surface.

BACKGROUND OF THE INVENTION

Human and animal health can be adversely affected by many microorganisms, including bacteria, yeasts, viruses, fungi, mold, and protozoa. Human and animal contact with microorganisms is known to cause a wide variety of diseases, illnesses, and ailments.

It is well known that the washing of hard surfaces (e.g. food preparation surfaces and surgical room equipment), food (e.g. fruits and vegetables), and skin (e.g. hands) with soap and water, can remove many microorganisms from those surfaces. Removal of microorganisms by hand washing with soap is largely due to a combination of the surfactancy of the soap and the mechanical action of the washing procedure. Because washing with soap is effective at removing a substantial number of microorganisms already present, but has only a minimal, if any, lasting or persistent effect on microorganisms that subsequently come into contact with the already washed hands, it is often recommended that people wash their hands frequently in order to reduce the spread of viruses, bacteria, and other microorganisms. Compliance with this recommendation is important for an individual's personal health and hygiene, but is especially important for individuals working in the health and food industries.

Antimicrobial cleansing products for the removal of microorganisms from surfaces, including skin, are available in a variety of types. The most common types utilized for personal hygiene and by personnel working in the health and food industries, include those containing soaps and those containing alcohol.

Traditional rinse-off disinfectant products, such as detergents and soaps, are generally effective at reducing the number of microorganisms present on a surface when proper procedures are employed. For example, Dial® liquid soaps containing triclosan, when used for hand washing, have been shown to reduce the number of bacteria present on the skin by about 2.0-2.5 orders of magnitude (99.0-99.7%) after one 30-second handwash, as measured by standard Health Care Personal Handwash Tests (HCPHWT). In other words, after washing, the washed skin is contaminated with only 0.3%-1.0% of the number of bacteria than was the unwashed skin before the 30-second handwash. Although, when used properly, soaps are capable of removing the majority of bacteria that are present, the persistence of any antimicrobial activity remaining on the surface is minimal, so immediately following hand washing, re-contamination of the hands begins to occur through contact with other contaminated surfaces. In addition, because these traditional rinse-off disinfectant products were developed for use in a washing procedure that uses a substantial amount of water; their use is limited to locations where a substantial amount of water is available.

Another commonly used type of disinfectant are those products containing relatively high levels of alcohol. Alcohol-based disinfectants result in the immediate removal or inactivation of a substantial portion of microorganisms present on the treated surface. Disinfectants based on alcohol, typically ethanol, have an additional advantage as disinfectants because alcohol readily evaporates from the skin at body temperature. Purell® is one example of a skin disinfectant that uses alcohol as the active ingredient. Although properly applied alcohol-based disinfectants are generally effective at removing or destroying bacteria that are present on the skin prior to application, immediately following treatment, re-contamination of treated skin begins to occur through contact with other contaminated surfaces.

Recent studies indicate that alcohol-based sanitizers with less than approximately 60% alcohol content may not be suitable to provide a desirable degree of antimicrobial activity, and alcohol contents above 95% are also less potent because proteins are not denatured easily in the absence of water ["*Hand Hygiene Revisited: Another Look at Hand Sanitizers and Antibacterial Soap*" SAFEFOOD NEWS—*Spring* 2004—Vol. 8 No. 3, Colorado State University Cooperative Extension].

Other water-soluble active ingredients have been used in skin disinfectants, instead of, or in combination with, alcohol. Birnbaum et al., (U.S. Pat. No. 6,441,045) disclose a water-soluble quaternary compound for use as a skin disinfectant. Beerse et al., (U.S. Pat. No. 6,217,887) disclose an antimicrobial composition for skin that is meant to be left-on rather than rinsed-off, which contains an antimicrobial active, an anionic surfactant, and a proton-donating agent, in a solution containing up to 98.85% water. Petersen et al., (U.S. Pat. No. 6,627,207) disclose a water-based, quick-drying, gel-type disinfecting composition having a low alcohol content (<30%). Osborne et al., (U.S. Pat. Nos. 5,776,430 and 5,906,808) describe a topical antimicrobial cleanser composition containing 0.65-0.85% chlorhexidine gluconate, or a pharmaceutically acceptable salt, and 50-60% denatured alcohol. Kross (U.S. Pat. No. 5,597,561) discloses water-based, adherent disinfecting composition directed at the prevention of microbial infections, which contains protic acid, a metal chlorite, and a gelling agent. Smyth et al., (U.S. Pat. No. 5,916,568) disclose a quick-drying hand sanitizer composed of alcohol, hydrogen peroxide, and an emollient to help prevent skin irritation. Sawan et al., (U.S. Pat. No. 6,180,584) disclose a disinfectant composition comprised of a polymeric, film-forming material and a metallic biocide in a carrier, which, when applied to a surface, forms a water-insoluble polymeric film on the surface in which the biocide is non-leachably bound to, complexed with, associated with, or dispersed.

Causton et al., (U.S. Pat. No. 5,869,600) disclose the use of water-insoluble, alcohol-soluble copolymers containing some level of quaternary ammonium groups for use as film-forming polymers utilized as antiperspirants.

Other approaches have employed methods that attach reactive silane-based quaternary ammonium compounds to particular substrates via a siloxane bond. For example, AEGIS Environments' product line includes products that utilize polymers of 3-(trimethoxysilyl)propyldimethyloctadecyl ammonium chloride, and are generally applied using alcohol-based solutions. According to product literature, AEM 5700 is 43% 3-(trimethoxysilyl) propyldimethyloctadecyl ammonium chloride in methanol, which can be used to coat the surface of textiles and other objects. This method results in the formation of a permanent covalent bond between the quaternary ammonium antimicrobial compound and the surface being treated. Removal of the applied antimicrobial is thus nearly impossible, even using alcohol-based solvents. Furthermore, the reactive trimethoxysilyl compounds are toxic and not suitable for use on skin.

Sawan (U.S. Pat. No. 6,264,936) describes an antimicrobial material which can be used to form on the surface of a substrate an antimicrobial coating or layer which kills microorganisms on contact. The antimicrobial coating or layer, characterized in the reference as "non-leaching," is a combination of an organic matrix immobilized on the surface of the substrate to having biocidal metallic materials associated with the matrix. When a microorganism contacts the coating or layer, the biocidal metallic material is transferred to the microorganism in amounts sufficient to kill it. Specifically, the metallic antimicrobial agent used is silver. Although this method purports to provide a "non-leachable" coating, the mere fact that the metallic antimicrobial agent "is transferred" to the microorganism is contrary to the common definition of non-leachable. Furthermore, it is known that although silver and silver salts have very low solubility, the mechanism of antimicrobial activity is dependent on a finite solution concentration of silver ions. Indeed, Sawan later (column 3, line 9) qualifies the above statement to read "substantially low leachables". In a preferred embodiment of Sawan's patent, the organic material comprises a polyhexamethylene biguanide polymer which is crosslinked with an epoxide, such as N,N-bismethylene diglycidylaniline, to form a crosslinked network or matrix. This crosslinking step is necessary to prevent dissolution of the matrix. The materials described by Sawan generally require a curing step, generally in the range of 80° to 120° C., which is unsuitable for many substrates, particularly human skin. Furthermore, the preferred organic matrix polymer (polyhexamethylene biguanide) is known to be toxic to human cells in high concentrations (see U.S. Pat. No. 6,369,289 B1). The use of silver as an antimicrobial agent also incurs some undesirable effects. One disadvantage to this approach is that certain bacteria have been able to develop resistance to silver. (Silver S., "*Bacterial silver resistance: molecular biology and uses and misuses of silver compounds.*" *FEMS Microbiology Reviews,* 2003; 27:341-353). Another disadvantage to this approach is that diffusing silver may be able to enter the wound and may potentially stain the skin. An additional disadvantage of silver is the high cost of the raw material. Similar approaches are described in U.S. Pat. Nos. 6,180,584; 6,126,931; 6,030,632; 5,869,073, 5,849,311; and 5,817,325.

There is a need for improved means and methods for disinfecting surfaces, not only for improved personal hygiene, but also to reduce potential sources of contamination in both health and food industries. With currently used non-persistent disinfectants, personnel in the health industry (e.g. doctors, nurses, and patients) and the food industry (e.g. food handlers, food preparers, cooks, and servers) must apply a disinfectant, such as soap, to their skin several, and sometimes 20 or more times, a day. Consequently, there exists a need, for personal hygiene and hygiene within the health and food industries, for a disinfectant that can effectively sanitize a surface and persist actively on that surface to combat microorganisms that subsequently come into contact with the treated surface.

The need for an effective, persistent surface disinfectant is felt in all aspects of the health industry. It is an aspect of the current invention that the invention would be useful to disinfect skin prior to surgery, injection, phlebotomy, and catheter insertion. Microorganisms present a threat to the health and safety of patients whenever the skin is penetrated, broken, or breached. For example, such pathogens may be a hazard during surgical procedures. Without adequate disinfection of the incision site prior to surgery, microorganisms present on the skin gain access to the incision during or following surgery and cause infection. To prevent such infections, it is critical to disinfect the incision site prior to surgery with a disinfectant that possesses a high antimicrobial activity and a broad spectrum of action. Since surgical procedures can last for many hours, it is also important that the initial disinfection of the incision site persists and provides sustained antimicrobial activity for an extended period of time. In the United States, the Food and Drug Administration requires that a pre-surgical skin disinfectant be capable of reducing the number of flora on dry skin areas, such as an abdomen, by at least 2.5 orders of magnitude or to levels that are too low for reliable quantification (less than about 25 cfu/cm$^2$). On moist skin, such as inguinal areas, the disinfectant must reduce the initial bacterial population by a minimum of 3.2 logs (1.5× 10$^3$ cfu/mL) and be able to maintain this level for at least four hours.

The need for an effective, persistent, and durable surface disinfectant is also felt in all aspects of the food industry, including food collection (e.g. sanitation of cow teats), food processing (e.g. slaughterhouses), food packaging (e.g. fish canneries), and food distribution (e.g. restaurants and food stores). It is an embodiment of the current invention that the composition would be useful wherever a person has food handling responsibilities and particularly useful wherever proper hygiene is made difficult because the same individual has both food handling and money handling responsibilities (e.g. deli shop cashiers and wait staff).

The ability of many organisms to develop resistance to antimicrobial compounds is a serious problem. Reports of rampant infections from organisms such as methacillin-resistant *Staph. aureus* (MRSA) abound in the news media. Such resistance is known to occur for many antibiotics, as well as for metal-based systems (such as silver). Quaternary ammonium compounds, on the other hand, do not promote development of resistant organisms.

SUMMARY OF THE INVENTION

The current invention provides a disinfectant composition comprising an alcohol-soluble, water-insoluble, antimicrobial polymer suitable for disinfecting and for providing a prolonged antimicrobial property to a variety of surfaces, including skin.

The invention provides a disinfectant composition, comprising an antimicrobial polymer in an alcohol- or glycol-containing solvent, wherein the antimicrobial polymer is readily soluble in the alcohol or glycol, but insoluble in water, and wherein the solvent serves as a carrier for applying said antimicrobial polymer to a surface, whereby said surface acquires a coating of the antimicrobial polymer.

It is an advantage of the invention that the antimicrobial polymer imparts a lasting antimicrobial activity to said surface.

It is an embodiment of the invention that the antimicrobial polymer is selected so that its antimicrobial activity occurs by virtue of a contact-killing mechanism, which does not require leaching, elution, or releasing into contacting fluids at levels that would result in fluid disinfection. Moreover it is preferred that the antimicrobial polymer does not appreciably leach, elute or release from the surface to which the antimicrobial composition is applied.

In particular embodiments of the invention the alcohol-containing solvent consists essentially of at least one alcohol selected from the group consisting of ethanol, methanol, and isopropanol. It is preferred that the alcohol content of the disinfectant solution is between 69% and 95% by weight.

In particular embodiments of this invention the alcohol-containing solvent consists essentially of at least one glycol selected from the group consisting of glycerol, ethylene glycol, propylene glycol, butylene glycol, pentane glycol, isomers and derivatives thereof, and mixtures of any of the aforesaid. It is preferred that the glycol content of the disinfectant solution is between 60% and 95% by weight.

In particular embodiments of this invention the alcohol-containing solvent consists essentially of a mixture of at least one alcohol and one glycol, wherein the alcohol is selected from the group consisting of ethanol, methanol, and isopropanol, and wherein the glycol is selected from the group consisting of glycerol, ethylene glycol, propylene glycol, butylene glycol, pentane glycol, isomers and derivatives thereof, and mixtures of any of the aforesaid. It is preferred that the alcohol-glycol mixture content of the disinfectant solution is between 60% and 95% by weight.

In particular embodiments of the invention the antimicrobial polymer may consist essentially of molecules that are derived or produced from at least one allyl- or vinyl-containing monomeric moiety. In some embodiments of the invention, the antimicrobial polymer consists essentially of molecules that are comprised of at least one quaternary-ammonium-containing monomeric moiety.

It is an embodiment of this invention that quaternary ammonium moieties are covalently bonded to the antimicrobial polymer, or attached to the molecular structure of the antimicrobial polymer by covalent chemical bonds, and are part of the polymer molecular structure, and that said quaternary ammonium moieties are located either in the main-chain of the polymer, or in side-groups of the polymer. Thus the quaternary ammonium moieties, alternatively may be the only moieties of the polymer structure, may be incorporated within the polymer structure, or may be attached to the polymer structure. "Main-chain" and "side-groups" are terms commonly used to describe polymer molecular structure and will be familiar to one skilled in the art.

Some of the antimicrobial polymeric molecules used in the present invention can be synthesized by step-growth polymerization, such as by the reaction of a difunctional alcohol with a diisocyanate to form a polyurethane polymer that contains at least one quaternary ammonium group in a monomeric moiety which is attached to the molecular structure of the polymer by covalent chemical bonding. Preferably, the number of quaternary ammonium groups in the polyurethane polymer will be at least one mole ($6.02 \times 10^{23}$) per 650 grams of polyurethane polymer. More preferably, the number of quaternary ammonium groups in the polyurethane polymer will be at least one mole ($6.02 \times 10^{23}$) per 350 grams of polyurethane polymer.

The antimicrobial polymeric molecules may have an average degree of polymerization of 5 to 25,000; preferably 50 to 10,000; and more preferably 100 to 5,000.

In one embodiment of the invention, the disinfectant composition is applied to a surface, which surface may be the skin of an animal, the skin of a human, a nonliving porous surface, or a nonliving nonporous surface.

For example, the disinfectant composition may be applied to skin of a human before a medical procedure. The term "medical procedure" includes, without limitation, surgery, injection, phlebotomy, and catheter insertion, and further includes other procedures that breach the skin. Furthermore, the disinfectant composition may be applied to the skin of an animal before a veterinary procedure. The term "veterinary procedure" includes, without limitation, surgery, injection, catheter insertion, and other procedures that breach the skin or hide of an animal.

In another embodiment of the invention, the disinfectant composition may be applied to the hands of health care workers to minimize transmission of microbes between infected patients or between infected sites on a patient.

In another embodiment of the invention, the disinfectant composition may be incorporated in cosmetic formulations to reduce or prevent microbial growth in the cosmetic.

An advantage of the invention is that many embodiments of antimicrobial polymer coating do not visibly stain the skin, and are colorless.

Another embodiment of the invention provides a disinfectant composition that contains a dye, enabling the coating to be visualized. In some embodiments, the dye is bonded to the antimicrobial polymer, thereby preventing migration of the dye from the coating.

An advantage of many embodiments of the invention is that, after the solvent has dissipated, the coating is generally odorless.

Many embodiments of the disinfectant composition have a pH between approximately 5 and approximately 9, preferably between 6.5 and 8.0.

Various embodiments of the disinfectant composition may be applied to the skin in a form selected from the group consisting of liquid, gel, foam, and aerosol.

Optionally, the disinfectant composition additionally contains at least one additive selected from the group consisting of a drug, an antimicrobial, an antiseptic, a thickening agent, a moisturizer, an emollient, a vitamin, a temporary dye, a permanent dye, and a UV absorber. When such an additive is an antimicrobial, it may be an alcohol, which also serves as a solvent for the antimicrobial polymer with persistent activity. The antimicrobial or antiseptic additive may also be a quaternary ammonium salt, a biguanide, or a phenolic compound. In a particular embodiment the added antimicrobial or antiseptic is a quaternary ammonium salt, such as benzalkonium chloride, benzethonium chloride, dimethyldidecyl ammonium chloride, or mixtures thereof. In another embodiment the added antimicrobial or antiseptic is a biguanide, such as chlorhexidine or poly(hexamethylene biguanide). In another embodiment, the added antimicrobial or antiseptic is a phenolic compound, such as phenol or triclosan. In some embodiments, the emollient is glycerol, ethylene glycol, propylene glycol, butylene glycol, pentane glycol, dipropylene glycol, polypropylene glycol, polyethylene glycol, mineral oil, a fatty alcohol, isopropyl palmitate, lanolin, derivatives of lanolin such as the ethoxylated acetylated alcohol and surface active alcohol derivatives of lanolin, squalane, fatty alcohols, glycerin, and silicones such as dimethicone, cyclomethicone, or simethicone, or mixtures thereof. In another embodiment, the drug is an antibiotic, anti-inflammatory, an analgesic, or an anesthetic agent.

In some embodiments, the antimicrobial polymer can be manufactured by mixing one species of monomer with at least one other different species of monomer, and copolymerizing the monomers, wherein at least one of the monomers bears at least one quaternary ammonium moiety, producing a copolymer that is readily soluble in alcohol and insoluble in water.

In some embodiments the antimicrobial polymer can be manufactured by polymerizing a monomer, wherein the monomer bears at least one quaternary ammonium moiety, producing a polymer that is readily soluble in alcohol and insoluble in water.

In another optional embodiment of the invention, a polymer is provided which contains both dye (e.g. fluorescein) and antimicrobial (e.g. quaternary ammonium) units both covalently bonded to the polymer molecular structure, or attached to the polymer molecular structure by covalent chemical bonds, and hence are part of the polymer molecular structure, and are located either in the main-chain of the polymer, or in side-groups of the polymer.

It is an embodiment of this invention to provide a polyurethane polymer which is readily soluble in a solvent consisting essentially of alcohol and/or glycol, but insoluble in water, and which contains at least one quaternary ammonium moiety attached to the molecular structure of the polymer by covalent chemical bonds, and which is capable of providing durable antimicrobial activity when applied to a surface.

It is an embodiment of this invention that there is no covalent chemical bond formed between the antimicrobial polymer and the substrate to which it is applied. Furthermore, the antimicrobial polymer may be removed from a substrate to which it has been applied by using alcohol, glycol, or a solvent having significant alcohol content.

It is an embodiment of this invention that metals or metallic salts are not used as antimicrobial agents.

It is an embodiment of this invention that a curing step is not required to impart insolubility to the antimicrobial polymer after it has been applied to a surface.

It is an embodiment of the invention that a portion, less than approximately 50% of the total polymer weight, of the antimicrobial polymer be soluble in water or aqueous fluids. This embodiment enhances the durable and quick-acting properties of the antimicrobial polymer. Enhancement of this activity can be achieved with lower molecular weight polymers.

It is an embodiment of the invention that the water-insoluble and the alcohol-soluble or glycol-soluble antimicrobial polymers of this invention may be utilized as components of polymeric devices including medical devices and household goods. The antimicrobial polymers of this invention may be utilized to produce films, fibers, gels, foams, adhesives, sealants, or caulks which may be incorporated in or used to form other articles, such as cosmetic formulations, sutures, or wound dressings.

Another embodiment of this invention is to provide a permanent antimicrobial treatment for synthetic sutures, such as medical sutures or multifilament polyester sutures.

Another embodiment of this invention is to provide an antimicrobial polymer which is water-insoluble and either alcohol-soluble or glycol-soluble which can be incorporated into hydrophilic polyurethane foam to be used as a non-leaching antimicrobial wound dressing.

It is an embodiment of this invention is to provide an antimicrobial polymer which is water-insoluble and either alcohol-soluble or glycol-soluble which can be incorporated into a UV-curable coating which can be applied to plastic films or sheets. The coated films and sheets can be further thermo-formed or vacuum-formed into antimicrobial products having a desired shape.

It is an embodiment of this invention to provide a method of disinfecting a substrate comprising the steps of treating the substrate with a solution of a water-insoluble antimicrobial polymer comprising quaternary ammonium moieties, wherein, the solvent and/or the polymer solution is capable of wholly or partially dissolving, absorbing-into, or otherwise penetrating the surface of the substrate; and drying the substrate to remove the solvent and to impregnate, infuse, coat, adhere, attach, or interpenetrate the antimicrobial polymer to the substrate wherein antimicrobial properties are imparted to the substrate and are not removed by exposure to aqueous fluids.

The substrate with polymer impregnated therein may comprise an interpenetrating network (IPN). The substrate may be a polymer which may be in a final-use form such as a film or fiber, or may be a polymer intended for subsequent use in a molding or shaping operation, such as one for making a resin, pellet, extrusion, or powder.

The substrate may also be a textile, wood, or paper. The substrate may be wholly or just partially infused with the polymer solution. In the case of partial infusion, the antimicrobial polymer will be deposited to a greater extent at, or just below, the surface of the substrate, as opposed to throughout the interior of the substrate. The substrate may be insoluble in the solvent used to prepare the antimicrobial polymer solution; however it is necessary that the solvent be capable of penetrating into the substrate material. For instance, some particular combinations of polymers and solvents may result in absorption of the solvent and polymer solution into the substrate without causing the substrate to dissolve.

The solvent may also be capable of dissolving the substrate either entirely or partially. For instance, a polymer solution capable of entirely dissolving the substrate may be applied to the substrate for a period of time sufficient to allow the surface of the substrate to be affected by the polymer solution, but not long enough for the substrate to be dissolved. In this manner, the surface of the substrate becomes modified with antimicrobial polymer.

An embodiment of this invention is to provide a solution comprising a water-insoluble antimicrobial polymer comprising quaternary ammonium moieties and at least one other polymer which are both dissolved in a solvent. A solution of an antimicrobial polymer (in alcohol or other solvent) may be combined with a solution of a different polymer, or a different polymer may be added to, or dissolved into, the antimicrobial polymer solution to form a compatible solution or mixture which may be further processed to prepare an article or object; formed or shaped into a film, tube, sheet, rod, fiber, coating, or powder; or used to treat a substrate.

DETAILED DESCRIPTION OF THE INVENTION

Definitions

As used herein, the following terms have the following meanings:

"Microbe" or "microorganism" refers to any organism or combination of organisms such as bacteria, viruses, protozoa, yeasts, fungi, molds, or spores formed by any of these.

"Antimicrobial" refers to the microbicidal or microbistatic properties of a compound, composition, article, or material that enables it to kill, destroy, inactivate, or neutralize a microorganism; or to prevent or reduce the growth, ability to survive, or propagation of a microorganism.

A "disinfectant" is an agent that destroys, neutralizes, or otherwise interferes with the growth or survival of microorganisms.

"Alcohol" means a volatile liquid having the formula $C_nH_{2n+2-x}(OH)_x$ where n is an integer from 1 to 10, and x is an integer from 1 to 3; and preferably where n is from 1 to 5, and x is 1 or 2; and more preferably where n is 2 or 3, and x is 1. The term "alcohol" as used herein encompasses monohydroxy alcohols (x=1) as well as glycols (x=2, 3) which have two or more hydroxyl groups. Preferred glycols are non-toxic.

"Soluble" means that the substance is capable of being dissolved in a quantity of a specified liquid, such as glycol, alcohol or water. Many polymers that are soluble in alcohol solvents are also soluble in glycol solvents.

"Readily soluble" means that the solute in question is virtually 100% soluble, capable of forming a solution at room temperature containing up to 20 wt % of the solute, in a specified solvent, e.g. a particular glycol, alcohol, or combinations of alcohols and glycols.

"Insoluble" means that the substance will not significantly dissolve in a large excess (e.g. >100-fold) of a particular solvent, e.g. water.

"Volatile" means that the solvent or liquid fully evaporates at room temperature.

"Durable" means insoluble in water, not easily removed by, for example, perspiration, incidental contact with aqueous fluids, or light washing with aqueous fluids.

"To impart" means to instill, to bestow upon, to transmit, to convey, or to otherwise incorporate a functional characteristic or property to a substrate. For example, a quaternary ammonium group may impart antimicrobial activity to a something.

"To combine" means to infuse, to coat, to adhere, to attach, to impregnate, to penetrate, to absorb, to mix, or to otherwise physically incorporate some substance into or onto a substrate.

A "non-hydrolyzable" bond is a chemical bond that does not hydrolyze under standard conditions to which the bond is expected to be exposed under normal usage of the material containing the bond. For example, the non-hydrolyzable bonds of a wound dressing or a suture according to the present invention would not undergo a hydrolysis-type reaction that results in the fission of such bonds under normal storage conditions such as exposure to wound exudates, body fluids, microbes, enzymes, antiseptic salves, creams, ointments, and other aqueous media in the normal physiological pH range.

"Contact-killing" means a property of killing microorganisms which does not require leaching, elution, or releasing into contacting fluids at levels that would result in fluid disinfection.

"Antimicrobial metallic material" means a metal, such as colloidal silver, or a metal salt, in a form capable of imparting antimicrobial activity to a composition. This invention provides antimicrobial activity in the absence of an antimicrobial metallic material.

"Substrate" is sometimes synonymous with "surface" and means any material in need of antimicrobial protection with which the compositions described herein may be used. The substrate may exist as an independent article separate from the composition and may comprise the skin of an animal, the skin of a human, a nonliving porous surface, or a nonliving nonporous surface. The surface may comprise a polymer, resin, powder, textile, wood, paper, skin, and may be a component of pellets, clothing, sutures, wound dressings, and various other articles. Alternatively, the composition may be incorporated with the substrate to form polymeric devices or objects including, for instance, films, fibers, sheets, gels, foams, adhesives, sealants, caulks, moldings, rods, tubes, medical devices, cosmetic formulations, and household goods.

One exemplary embodiment of the current invention utilizes an antimicrobial polymer having polymeric molecules that are composed of one type of monomeric moiety; alternatively, the polymeric molecules may be composed of more than one type of monomeric moiety. In exemplary embodiments of the current invention, the quaternary ammonium groups of the monomeric moieties impart antimicrobial activity to the polymeric molecules. Desirably, such monomeric moieties, which comprise quaternary ammonium groups, constitute at least 2% by weight of the polymeric molecules, more preferably at least 10% of the polymeric molecules, and most preferably at least 25% of the polymeric molecules. Preferably, the number of quaternary ammonium moieties in the antimicrobial polymer will be at least one mole ($6.02 \times 10^{23}$) per 650 grams of polymer. More preferably, the number of quaternary ammonium moieties in the antimicrobial polymer will be at least one mole ($6.02 \times 10^{23}$) per 350 grams of polymer.

It is an embodiment of this invention that quaternary ammonium moieties are covalently bonded to the antimicrobial polymer, or attached to the molecular structure of the antimicrobial polymer by covalent chemical bonds, and are part of the polymer molecular structure, and that said quaternary ammonium moieties are located either in the main-chain, also described as the backbone, of the polymer, or in side-groups of the polymer. Thus the quaternary ammonium moieties, alternatively may be the only moieties of the polymer structure, may be incorporated within the polymer structure, or may be attached to the polymer structure. "Main-chain" and "side-groups" are terms commonly used to describe polymer molecular structure and will be familiar to one skilled in the art. Groups within the main-chain of the polymer are also described as being within the "backbone" of the polymer. Groups that are side groups are also described as being "pendant" to the backbone of the polymer chain.

In a preferred embodiment of this invention, the quaternary ammonium moieties of the antimicrobial polymer are contained in the main chain or backbone of the polymer backbone, rather than pendant to the polymer backbone.

In a preferred embodiment of this invention, the quaternary ammonium moieties of the antimicrobial polymer are connected to the polymer molecular structure by stable chemical structures and covalent bonds that are non-hydrolyzable. Examples of hydrolyzable bonds or structures include esters, amides, and anhydrides. Examples of bonds and structures that are non-hydrolyzable include urethanes, ureas, ethers (C—O—C), carbon-carbon (C—C), and carbon-nitrogen (C—N) bonds.

The antimicrobial polymer is formulated to be insoluble in water and readily soluble in aqueous solutions of at least 75 wt % of an alcohol, glycol, or mixture thereof. More preferably it is formulated to be insoluble in water and is readily soluble in such solutions of at least 50 wt % of an alcohol, glycol, or mixture thereof, and most preferably it is formulated to be insoluble in water and readily soluble in solutions of at least 25 wt % of an alcohol, glycol, or mixture thereof. It is an embodiment of the current invention that the antimicrobial polymer can be applied to surfaces, including skin, dissolved in an alcohol-containing solvent.

The relative solubility of polymers in different solvents is not trivial. This invention pertains to polymers that are soluble in alcohol and glycols, yet insoluble in water. This specific combination of properties is manifested in only a relatively small number of the many different types of known natural and synthetic polymers. Polymers may generally be divided into two groups: water-soluble, and water-insoluble. Some water-insoluble polymers may be soluble in various organic solvents. Solubility generally depends on the properties of the particular polymer-solvent combination, with soluble combinations resulting when the chemical structures of the polymer and solvent are similar. Polarity of the solvent is perhaps the most important consideration. Polarity of some common solvents in order of most polar to least polar are: water, ethanol, ether, toluene, and hexane. Many water-soluble polymers are also soluble in alcohol. Among the alcohols, the polarity decreases in the order of methanol, ethanol, and isopropanol, with the polarity of methanol being closest to that of water. Thus, many water-soluble polymers are more soluble in methanol, than in ethanol or isopropanol. Ethanol, isopropanol and non-toxic glycols are preferred solvents for the practice of this invention. Isopropanol is not generally a very good solvent for most polymers. Even polyethylene oxide, which is highly soluble in water, is insoluble in isopropanol, as are many other water-soluble polymers such as polyDADMAC, alginate, polyacrylate, and even poly(vinyl alcohol). The vast majority of both natural and synthetic polymers are not soluble in isopropanol. The further requirement that the polymer also be insoluble in water makes the selection of useful polymers for the practice of this invention even more critical.

The alcohol-containing or glycol-containing solvent may serve a two-fold purpose, not only as a carrier, but also as an immediate disinfectant. After the alcohol-containing or glycol-containing solvent has evaporated, absorbed, or dissipated, a coating of the antimicrobial polymer remains on the skin or other substrate. This coating is durable, and because it is insoluble in water, it is not easily removed by, for example, perspiration, incidental contact with aqueous fluids, or light washing with aqueous fluids.

It is an embodiment of the current invention that an alcohol is used as solvent and carrier, including, but not limited to, ethanol, methanol, isopropanol, and mixtures thereof. It is an embodiment of one exemplary embodiment of the invention that the alcohol solvent is denatured alcohol, specifically Denatured Alcohol SDA 3-C, which is a commercial, non-beverage grade, denatured alcohol defined by the Alcohol and Tobacco Tax Division of the Internal Revenue Service as ethanol with a 5% isopropanol denaturant (i.e., 95% ethanol/5% isopropanol).

It is an embodiment of the current invention that a glycol is used as solvent and carrier, including, but not limited to glycerol, ethylene glycol, propylene glycol, butylene glycol, or pentane glycol. Various isomers and derivatives of glycerol, ethylene glycol, propylene glycol, butylene glycol, and pentane glycol are also suitable solvents for the invention. For example, the family of pentane glycols includes 1,4-pentanediol, 1,5-pentanediol, 2,4-pentanediol, and another isomers. Other derivatives of glycols may be suitable solvents for the invention. For example, a halogenated glycol may be employed in an appropriate embodiment of the invention.

Glycols are generally not as volatile as lower alcohols (such as ethanol); however, may still have utility as a solvent/carrier for the antimicrobial polymers of the current invention. For instance, propylene glycol may be used as a solvent/carrier when the antimicrobial polymer is incorporated into a cosmetic formulation for application to the skin. The propylene glycol may absorb into the skin, rather than evaporating, thus leaving a persistent antimicrobial polymer coating. This approach avoids possible undesirable effects of using lower alcohols (such as skin irritation, drying of skin, or flammability).

It is an embodiment of the current invention that a mixture comprising an alcohol and a glycol is used as solvent and carrier. The alcohol component of the mixture may include, but is not limited to, ethanol, methanol, isopropanol, and mixtures thereof. The glycol component of the mixture may, for example be glycerol, ethylene glycol, propylene glycol, butylene glycol, pentane glycol, or an isomer or derivative thereof, or mixture of any of the aforesaid. It is preferred that the combined alcohol-glycol content of the disinfectant solution mixture is between 60% and 95% by weight.

The antimicrobial polymer may also be soluble in other organic solvents such as acetone, methyl ethyl ketone, tetrahydrofuran, ethyl acetate, ethers, esters, benzene, toluene, carbonates, hydrocarbons, or chlorinated hydrocarbons, and solutions of the antimicrobial polymer in any of these solvents may be used to prepare the antimicrobial composition; however, these solvents may not necessarily provide the advantage of immediate disinfection such as provided by alcohols or glycols.

It is a feature of this invention that the antimicrobial properties are permanently locked into the polymer structure. This can be accomplished, for example, by incorporating chemical functionalities with antimicrobial properties directly into the molecular structure of the polymer. This provides not only durability and persistence of antimicrobial effect, but also prevents soluble antimicrobial components, e.g. those of low molecular weight, from leaching from the antimicrobial coating and entering the substrate, or migrating to areas where it is not desirable to have antimicrobial activity. For example, when applied to skin, the composition will provide persistent antimicrobial activity; however, antimicrobial activity will not migrate from the polymer and penetrate the skin surface or enter into cells where it may have undesirable effects, after evaporation of the alcohol-based carrier solvent.

It is an advantage of the current invention that the composition would be useful to protect individuals at risk of contacting biological warfare agents (e.g. military personnel and postal workers), either by treating their skin or by treating the surfaces of equipment and materials that these individuals contact.

It is an embodiment of the current invention that a composition of the present invention may be used on animal skin (e.g. sanitization of cow teats, surgical procedures, and veterinary procedures).

An advantage of this invention is that it utilizes quaternary ammonium compounds as the active antimicrobial agent, and quaternary ammonium compounds do not promote the development of resistant organisms such as MRSA or VRE. Examples are provided below to demonstrate the efficacy of the materials of the current invention against such organisms.

The disinfectant composition of the present invention may additionally contain other inert or active ingredients. For example, thickening agents may be included in order to increase viscosity or to provide a gel form of the product. Additives, such as moisturizers, emollients, vitamins, UV absorbers, drugs, antimicrobials, or other inert and active agents, may also be added. Such additives do not need to be water-insoluble, as they may serve their purpose by acting transiently or otherwise may be entrapped in the polymeric coating and thereby stabilized against easy removal by aqueous fluids. In addition, permanent or temporary dyes may be added to the composition, or alternatively applied to the polymeric coating after it has been applied to the surface, in order to serve as a visual indicator of the presence of the polymeric coating.

Although the composition of the current invention provides a polymer film or coating with non-leaching antimicrobial properties, it may be desirable in some circumstances to incorporate an additional antimicrobial or antiseptic agent into the composition in order to provide additional efficacy. This additional agent is not covalently bonded to the polymer, and thus may be leachable. This does not alter the non-leachable nature of the previously-described antimicrobial polymer. When the additional antimicrobial agent has been fully leached from the composition, the antimicrobial polymer will still provide non-leachable antimicrobial activity. Furthermore, the antimicrobial polymer matrix can serve to slow the leaching rate of the additional agent, thus prolonging the efficacy of the added agent. Examples of useful antimicrobial or antiseptic additives include quaternary ammonium salts, biguanides, and phenolic compounds. In certain embodiments the added antimicrobial or antiseptic is a quaternary ammonium salt, such as benzalkonium chloride, benzethonium chloride, dimethyldidecylammonium chloride, or mixtures thereof.

In another embodiment the added antimicrobial or antiseptic is a biguanide, such as chlorhexidine or poly(hexamethylene biguanide). In another embodiment, the added antimicrobial or antiseptic is a phenolic compound, such as phenol or triclosan.

It is an embodiment of the current invention that the composition may be formulated as a liquid, gel, foam, or aerosol spray and may be applied to a surface, including the skin of a human or other animal, in order to achieve a prolonged antimicrobial effect.

The examples that follow demonstrate the synthesis and application of glycol-soluble, alcohol-soluble, water-insoluble, antimicrobial polymeric molecules. It is an embodiment of the invention that these polymeric molecules can be synthesized by free radical vinyl polymerization of, generally, a mixture of two different monomers, a first monomer (A) and a second monomer (B), at least one of which contains quaternary ammonium groups. The first monomer (A), and homopolymers of monomer A, are generally water-soluble, while the second monomer (B) is generally water-insoluble. A mutually effective solvent (such as alcohol or glycol) for monomers A & B may be used to prepare a homogeneous solution suitable for copolymerization of the two monomers. The copolymer of A+B, is soluble in alcohol or glycol. It should be understood that this is just one possible illustrative method to formulate the composition and one skilled in the art will realize that there are numerous other methods that can be used to prepare the alcohol-soluble, water-insoluble, antimicrobial polymeric molecules. Mixtures of three or more monomers may also be used to prepare suitable antimicrobial copolymers.

It is an embodiment of this invention that the polymeric molecules can be synthesized by step-growth polymerization, such as by the reaction of a difunctional alcohol with a diisocyanate to form a polyurethane polymer. It is an embodiment of this invention that other types of step-growth polymers may also be utilized including, but not limited to, polyamides (nylons), polyesters, and polyureas. The incorporation of the antimicrobial moiety into the polymer may be accomplished by utilizing an antimicrobial compound with reactive functionality. For instance, Akzo Nobel offers a range of compounds sold under the trade-name of Ethoquad. An example is Ethoquad C/12-75DK, which is a methyl/C12 quaternary ammonium compound with two reactive hydroxyethyl substituents that can be reacted with a diisocyanate such as tolylene-2,4-diisocyanate (TDI) to form an antimicrobial polyurethane polymer which contains quaternary ammonium moieties in the polymer main-chain structure.

In one embodiment of this invention, a dye molecule may be incorporated into, or covalently bonded to, the antimicrobial polymer structure in order to provide a nonleaching visible marker for the composition. For instance, the fluorescein dye molecule contains two hydroxyl groups which may be reacted with a diisocyanate to form part of a polyurethane structure. When a mixture of fluorescein and Ethoquad C/12-75DK is reacted with TDI, the resulting polymer contains both dye (fluorescein) and antimicrobial (quaternary ammonium) units in the polymer main-chain structure.

The antimicrobial moieties may also be incorporated into the polymer after formation of the polymer. This can be achieved, for example, by transesterification or other substitution reactions, such as the reaction of Ethoquad with a polyacrylate.

The polymer molecules synthesized will have an average degree of polymerization of 5 to 25,000 (monomeric moieties per molecule), but more preferably 50 to 10,000, and most preferably 100 to 5000. Suitable vinyl monomers for use in generating the polymer include, but are not limited to, allyl-containing monomers, vinyl-containing monomers, styrene derivatives, allyl amines, ammonium salts, acrylates, methacrylates, acrylamides, methacrylamides, dimethylaminoethyl methacrylate (methyl chloride quaternary), dimethylaminoethyl methacrylate (benzyl chloride quaternary), dimethylaminoethyl acrylate (methyl chloride quaternary), dimethylaminoethyl acrylate (benzyl chloride quaternary), and other compounds with the structure $CH_2=CR-(C=O)-X-(CH_2)_n-N^+R'R''R'''//Y^-$ (where R is hydrogen or methyl, n equals 2 or 3, X is either O, S, or NH, R', R", and R''' are independently selected from the group consisting of H, C1 to C16 alkyl, aryl, arylamine, alkaryl, and aralkyl, and $Y^-$ is an anionic counterion to the positive charge of the quaternary nitrogen; diallyldimethylammonium salts; vinyl pyridine and salts thereof; and vinylbenzyltrimethylammonium salts).

Suitable free radical initiators for use in generating the polymer include, but are not limited to, azo compounds, such as AIBN and related compounds, and peroxides, such as benzoyl peroxide, dicumyl peroxide, t-butyl hydroperoxide, sodium persulfate, hydrogen peroxide, sodium peroxide, and other peroxides and hydroperoxides commonly used as free radical polymerization initiators. Photoinitiated polymerization may also be used wherein a suitable photoinitiator (e.g. a benzophenone derivative) is used which initiates polymerization upon exposure to light. Radiation polymerization may also be used, wherein polymerization is initiated by exposure to ionizing radiation (e.g. gamma rays).

Various testing methods may be employed to measure the antimicrobial efficacy of the antimicrobial polymers and compositions described herein. The "Carrier Persistence Test", or CPT, is described below. The compositions and materials of this invention have been found to give excellent results when tested by the CPT. Reductions of bacterial populations generally exceed 6 logs (99.9999% reduction of viable organisms). The materials described by this invention are capable of producing a 3-log reduction of bacteria when tested using the CPT method. Preferably, the materials described by this invention are capable of producing a 4-log reduction of bacteria when tested using the CPT method. More preferably, the materials described by this invention are capable of producing a 5-log reduction of bacteria when tested using the CPT method. Still more preferably, the materials described by this invention are capable of producing a 6-log reduction of bacteria when tested using the CPT method. It should be understood that the CPT is a comparative test in which the antimicrobial materials are compared to control materials not treated with antimicrobial agent. The maximum theoretical log reduction obtainable in a particular CPT test is limited by the growth of the bacterial population on the untreated control. Thus, it is possible to obtain virtually 100% elimination of viable organisms even though the actual log reduction is below a specified number.

In some applications of the current invention it may be desirable that a portion (less than approximately 50% of the total polymer by weight) of the antimicrobial polymer be soluble in water or aqueous fluids. In this manner, the combined benefits of quick-acting antimicrobial efficacy from a soluble antimicrobial component, and prolonged durable antimicrobial activity from the insoluble antimicrobial polymer may be realized. This may be accomplished, for instance, by incorporation of hydrophilic units in the polymer structure in order to provide a degree of water-solubility to a portion of the polymer. For instance, hydrophilic —$CH_2$—$CH_2$—O—$CH_2$—$CH_2$— units may be incorporated into a polyurethane-based antimicrobial polymer by reacting bis(2-hydroxyethyl) ether with TDI. Enhancement of water-soluble or leachable antimicrobial content may also be achieved by preparing an antimicrobial polymer with a reduced molecular weight (smaller average degree of polymerization). Methods to reduce polymer molecular weight or degree of polymerization will be familiar to one skilled in the art.

In addition to their use as coatings, the alcohol-soluble/water-insoluble antimicrobial polymers of this invention may also be utilized as components of polymeric devices or objects including, for example, medical devices and household goods. This may be accomplished, for instance, by blending the antimicrobial polymer, or solutions thereof, with other polymers or solutions thereof, or polymerizable monomers or prepolymers, or solutions thereof. The antimicrobial polymers of this invention may also be used to form films, fibers, gels, foams, adhesives, sealants, and caulks which may be used as components in medical devices, polymeric devices, or other objects.

One embodiment of this invention is to provide a permanent antimicrobial treatment for synthetic sutures that will remain in the body, such as multifilament polyester sutures like Mersilene (uncoated) and Ethibond Excel (polybutylate coated), both sold by Ethicon. These sutures would help prevent significant threats, such as deep wound postoperative infection contributing to the complication after cardiac surgical procedures (Immer F F, Durrer M, Muhlemann K S, Erni D, Gahl B, Carrel T P. "*Deep sternal wound infection after cardiac surgery: modality of treatment and outcome*". Ann Thorac Surg. 2005 September; 80(3):957-61). According to the literature, the incidence of deep sternal wound infection varies between 1% and 3%. The bacterial spectrum demonstrated by several studies identified infection primarily by *S. aureus* (41.8%) and coagulase negative *Staphylococcus* (32.7%). Due to the morbidity associated with infection, it is also desirable to provide protection from blood-transmitted infections by having the sutures remain antimicrobial.

Another embodiment of this invention is to provide an alcohol-soluble/water-insoluble antimicrobial polymer which can be incorporated into hydrophilic polyurethane foam to be used as a wound dressing with non-leaching antimicrobial activity.

Another embodiment of this invention is to provide an alcohol-soluble/water-insoluble antimicrobial polymer which can be incorporated into a UV-curable coating system to impart non-leaching antimicrobial efficacy to the cured coating. This UV curable coating can be applied to plastic film which can subsequently be thermo-formed or vacuum-formed to a product with a desired shape.

Another embodiment of this invention is to provide an alcohol-soluble/water-insoluble antimicrobial polymer which can used as a component of an adhesive, such as an adhesive used to secure medical devices to skin, thereby providing an antimicrobial property to said adhesive.

EXAMPLES

The following Examples are provided to illustrate the invention and teach those skilled in the art how to make and how to use the subject matter. They are not to be read as limiting the scope of the invention.

Example A1

Co-Polymerization of (2-(methacryloyloxy)ethyl) Trimethylammonium Chloride and Butyl Methacrylate A solution was made by dissolving 2.5 grams of quaternary vinyl monomer (2-(methacryloyloxy)ethyl)trimethylammonium chloride 75% aqueous solution (Aldrich Chemical Co.)), 7.5 grams of butyl methacrylate (Aldrich Chemical Co.), and 0.1 gram or AIBN (2,2'-azobis(2-methylpropionitrile) (Aldrich Chemical Co.) in 10 grams of ethanol. The solution was sparged for 60 seconds with argon gas to expel dissolved oxygen and then sealed in a glass vial under an argon atmosphere. The vial was placed in a 70° C. oven for 24 hours. The copolymer containing solution was then diluted in ethanol (1:25).

Example A2

Application of the Composition to Skin

Approximately 1 mL of the solution generated in Example A1 was placed on the skin on the back of the hand of a human volunteer, then spread and rubbed with a gloved finger until dry. After drying, an inconspicuous film remained, which was not sticky or tacky, and was virtually imperceptible to the volunteer. Bromthymol blue (BTB) indicator dye is known to bind strongly to quaternary ammonium compounds. To visualize the presence of the polymeric coating, the area of the hand to which the polymer-containing solution was applied was rinsed with a 0.5% aqueous solution of BTB indicator dye adjusted to a pH 10. The hand was rinsed under tepid running tap water for 30 seconds with light digital manipulation to remove excess BTB indicator dye solution. The area of skin treated with the copolymer solution exhibited a blue/green color, while the surrounding skin did not, indicating presence of the applied polymer. Only after vigorous scrubbing with a detergent solution, was the coating diminished to the extent that the BTB indicator dye assay no longer indicated the presence of the polymeric coating.

Example A3

Co-Polymerization of (Vinylbenzyl)Trimethylammonium Chloride and Butyl Methacrylate (H-1)

A solution was made by dissolving 2.5 grams of quaternary vinyl monomer (vinylbenzyl)trimethylammonium chloride (Aldrich Chemical Co.), 7.5 grams of butyl methacrylate (Aldrich Chemical Co.), and 0.1 grams of AIBN (2,2'-azobis (2-methylpropionitrile) (Aldrich Chemical Co.), in 20 grams of methanol. This solution was sparged for 60 seconds with argon gas to expel dissolved oxygen, and then sealed in a glass vial under an argon atmosphere. The vial was placed in a 70° C. oven for 24 hours. The copolymer containing solution was then diluted in ethanol (1:2). This composition was designated as "H-1" and is referred to in subsequent examples.

Example A4

Application of the Composition to Polypropylene

The solution generated in Example A3 was used to coat the interior surface of several 15 mL polypropylene centrifuge tubes by filling them with the solution and leaving them filled overnight. The solution was then poured off and the alcohol was evaporated completely in a low temperature oven set to 50° C. To visualize the presence of polymeric coating on the inside of the tubes, approximately 5 mL of 0.5% aqueous solution of BTB indicator dye was added to one of the tubes and then shaken to coat the entire inside of the tube. After rinsing the tube several times with distilled water, the interior surface of the tube remained a deep blue color, indicating that the inner surface of the tube was coated with water-insoluble polymer.

Example A5

Antimicrobial Activity of Polymeric Composition

A 2 mL aliquot of a $10^{-4}$ dilution of an overnight culture of *S. aureus* (~$1 \times 10^8$ CFU/mL) was added to one polypropylene centrifuge tube treated as in Example A4 (sample) and to one untreated polypropylene centrifuge tube (control). During overnight incubation at 37° C., the tubes were slowly rolled to ensure contact between the bacteria culture and the interior surface of the tubes. The next day, serial dilutions of the bacteria cultures harvested from each tube were streaked onto bacteria culture plates. The culture harvested from the untreated control tube yielded $2.5 \times 10^4$ CFU, while zero colonies were observed on plates streaked with cultures harvested from the treated sample tubes. The difference in the number of colonies enumerated translates into at least a 4.4 log reduction in the bacterial population.

Example A6

Synthesis of a Quaternary Ammonium Polyurethane (H3-C) that is Soluble in Alcohol, but Insoluble in Water Fifty grams of Ethoquad C/12-75DK (Akzo Nobel) was placed in a round-bottom flask on a rotary evaporator and evaporated to dryness. The residue (37.5 grams) was redissolved in 70 mL tetrahydrofuran (THF) with agitation at approximately 50° C. Forty grams of tolylene-2,4-diisocyanate (TDI) was added and the solution was mixed for one hour while immersed in a water bath held at ~50° C. The viscosity of the solution increased during this time, and the solution remained clear when cooled to room temperature. The solution was stored overnight at room temperature and some additional increase in viscosity was observed. Nine grams of dipropylene glycol was added, and the solution was mixed for four hours at 50° C. The mixture was then placed on a rotary evaporator to remove all volatile solvent (primarily THF) by vacuum stripping at ~50° C. The mixture was then dissolved in 100 mL of isopropanol, and the vacuum stripping was repeated. The mixture was then dissolved in 100 mL of isopropanol once again, and the vacuum stripping was again repeated. The mixture was then redissolved in 100 mL of isopropanol to give a clear, viscous, yellowish solution with a solid polymer content of 56 wt %. The polymer solution was subsequently diluted to various concentrations ranging from 1% to 10% solids, and these solutions were used to coat various objects such as glass slides and polypropylene test-tubes. The coatings were clear to slightly opaque when dry, were non-tacky, and were adherent to the substrate. Furthermore, the coatings were not removed by rinsing in water or saline solution. The product polymer is believed to comprise a linear polyurethane with quaternary ammonium units in the main-chain structure of the polymer. The product of this example was coded as "H3-C", and is used as an antimicrobial coating in some of the following examples.

Example A7

Synthesis of a Quaternary Ammonium Polyurethane (H3-F) Containing Covalently-Bonded Fluorescein Moieties, which is Soluble in Alcohol, but Insoluble in Water Fifty milligrams of fluorescein dye (neutral molecule) was dissolved in 3 mL of THF, and then mixed with eight grams of tolylene-2,4-diisocyanate (TDI). This solution was mixed for one hour at ~50° C., and then stored overnight at room temperature before being mixed with ten grams of Ethoquad C/12-75DK (Akzo Nobel), which had previously been vacuum stripped to remove the isopropanol solvent and redissolved in 14 grams tetrahydrofuran (THF) with agitation at approximately 50° C. This mixture was then mixed for several hours at ~50° C., and then subjected to vacuum stripping. The mixture was redissolved in isopropanol and then vacuum stripped. The dissolution/stripping was repeated one additional time, and the product was dissolved in ~50 mL isopropanol. The solution was found to have a solids content of 17.4 wt %. The product of this reaction is expected to be fluorescein-labeled linear polyurethane containing quaternary ammonium moieties in the polymer main-chain structure. Additionally, the polymer is expected to contain fluorescein moieties in the polymer main-chain structure. The fluorescein moieties provide a useful diagnostic tool to measure the presence, dispersion, persistence, and migration of the polymer. Coatings were prepared on various substrates as described in the preceding example, and the coatings had similar properties to those described above. Coated glass microscope slides were placed into 50 mL culture tubes containing either 15 mL of deionized water or 15 mL of phosphate buffered saline and place in a shaking incubator for several hours at 37° C. The solutions were then analyzed by visible spectroscopy (Spectronic 20) at 495 nm. No leaching of fluorescein could be detected, indicating complete incorporation of the dye into the polymer structure.

Example A8

Preparation of an Antimicrobial Coating Composition

Appropriate amounts of the quaternary polyurethane described above (H3-C) and glycerol were diluted in isopropanol to give a composition that contained 10 wt % H3-C and 5 wt % glycerol. The solution remained clear, and the film forming and adherent properties of the polymer were not adversely affected when coatings were prepared on glass slides.

Example A9

Preparation of an Antimicrobial Coating Composition Containing a Skin Emollient (SS-1C)

Appropriate amounts of the quaternary polyurethane described above (H3-C of Example A6) and glycerol were diluted in isopropanol in order to give a final composition that contained 10 wt % H3-C, 5 wt % propylene glycol, and 5% dipropylene glycol, with the balance being isopropanol (80 wt %). The solution remained clear, and the film forming and adherent properties, as well as the antimicrobial efficacy of the polymer were not adversely affected when coatings were prepared on glass slides or pig skin. Propylene glycol and dipropylene glycol are known to have emollient properties and are widely used in topical skin products such as lotions and cosmetics.

Example A10

Preparation of an Antimicrobial Coating Composition Containing a Skin Emollient

The formulation of Example A9 (SS-1C) was diluted with isopropanol at ratios of one part SS-1C to one part isopropanol, and one part SS-1C to three parts isopropanol.

Example A11

Preparation of an Antimicrobial Coating Composition Containing a Skin Emollient and UV Absorber The formulation of Example A9 (SS-1C) is modified to include UV-absorbing or UV-blocking sunscreen ingredient in order to protect the skin from absorption of UV rays and to prevent sunburn. The UV-absorbing or UV-blocking additive is selected from the list comprising: para-aminobenzoic acid (PABA), PABA esters, cinnamates, benzophenes, salicylates, octocrylene, dibenzoyl-methane, avobenzone, oxybenzone, zinc oxide, and titanium dioxide.

Example A12

Preparation of an Antimicrobial Coating Composition Containing a Skin Emollient and Vitamin E The formulation of Example A9 (SS-1C) is modified to include 1% vitamin E. Vitamin E is practically insoluble in water, but freely soluble in alcohol.

Example A13

Preparation of an Antimicrobial Coating Composition Containing an Antimicrobial Additive (SS1C-BAC3)

An antimicrobial coating composition (SS1C-BAC3) is prepared by mixing 1.1 grams of benzalkonium chloride with 35.5 grams of the formulation of Example A9 (SS-1C). The benzalkonium chloride fully dissolved and the solution was clear and colorless. This composition was tested for antimicrobial efficacy using a modified version of ASTM test method #E 1874-97 ("*Standard Test Method for Evaluation of Antibacterial Washes by Cup Scrub Technique*"), as described below. Variations included using harvested pig skin from a slaughterhouse rather than live human volunteers. In addition to the SS1C-BAC3 material, a placebo was formulated which consisted of 5% propylene glycol and 5% dipropylene glycol in isopropanol. Results are presented below.

Summary and Results of Modified Cup Scrub Technique for Pig Skin
1. Preparation and Sterilization of Pig Skin Samples
    1.1 Nine total samples were used in this method—3 samples for test product (SS1C-BAC3), 3 for placebo, and 3 for negative controls. The samples were cut out of a sheet of pig skin by tracing the bottom of a Petri dish onto the skin and cutting out the circular piece, so that the samples were an appropriate size to completely line the bottom of the Petri dish. Each of the 9 samples were cut from the sheet of skin and placed into the bottom of its own Petri dish, stratum corneum side up.
    1.2 Once in the Petri dishes, the sample skins were wiped with a towel that was thoroughly saturated with 70% alcohol, and then placed under UV light in the BSC (biological safety cabinet) to dry for approx 10 minutes. The lids of the Petri dishes were also placed (facing up) along side of the samples under the UV light.
2. Application of Test Product and Placebo
    2.1 After drying under UV light, the BSC was switched to fluorescence with the blower on, and a 1×1 in square was drawn on to each of the skins with an ink marker. This is used as the site of application. The UV light was turned on again, with the lids still facing up, for a few minutes to insure that no contamination occurred while marking the skins.
    2.2 The BSC was switched back to fluorescence with the blower on, and the lids were placed back onto the Petri dishes containing the samples.
    2.3 One sample at a time, the lid was lifted from the Petri dish and 0.5 mL each of the test product was applied to the first three samples (within the designated square). The sterile pipette tip was changed in between each application.
    2.4 Step 2.2 is repeated 3 times with the placebo, and the remaining 3 sample skins are left as negative controls.
3. Performance of Cup Scrub Technique
    3.1 Once the product and placebo was applied each of the 9 samples were left covered in the BSC, and one sample was brought out at a time for testing.
    3.2 The cup (about 1.5 cm diameter and 1.5 in tall) was centered onto the application site of the sample with firm pressure to form a cup/skin seal. The cup was first sterilized in 95% alcohol and then flame dried. While one person maintained constant pressure on the cup to protect the cup/skin seal, another person dispensed 0.25 mL of inoculum into the cup. Once dispensed, the inoculum was left for a 5 minute exposure.
    3.3 After 5 minutes, a glass rod that had been sterilized in 95% alcohol and flame dried was used to scrub around the skin within the cup for 30 seconds. After the 30 seconds the fluid was recovered with a sterile pipette into 0.5 mL of neutralizer.
    3.4 Once the sample fluid was recovered, 0.25 mL of neutralizer was dispensed onto the same test site for a second recovery, and another 30 sec scrub was performed with a newly fired glass rod. The fluid was recovered into the same solution from the first scrub.
    3.5 Steps 3.2-3.4 are repeated for the remaining 8 samples.
4. Data Collection
    Results were quantified by making standard serial dilutions of the recovered scrub fluids and then plated using the spread plate technique. Plates were incubated over night and log reductions were calculated for both the negative control and the placebo 5. Results In tests of the antimicrobial coating composition (SS1C-BAC3) vs *E. coli*, two consecutive performances showed full kill, which corresponded to an average 4.5 log reduction in this instance of viable bacteria.

The placebo showed no effect on the test organism.

Example A14

Synthesis of a Quaternary Ammonium Polyurethane that is Soluble in Alcohol, but Insoluble in Water, and which has Flexible Hydrophobic Units Incorporated within the Molecular Structure (SS50H)

The method of Example A6 was substantially followed; however, a equimolar (1:1) mixture of 1,6-hexanediol and Ethoquad was used instead of Ethoquad. The resulting polymer was found to be water insoluble, and at least partially immiscible with isopropanol; however, it was completely soluble in ethanol. A solution of this polymer in ethanol (40.6 wt % polymer) was added dropwise to a large excess of distilled water with vigorous stirring. The precipitated polymer was collected by filtration and dried in a vacuum oven. The resulting dry polymer constituted over 85% recovery of the original material, despite the observation of considerable loss of precipitated material during filtration, drying, and recovery. This demonstrates that the polymer is significantly insoluble in water. Additionally, this type of reprecipitation treatment is expected to remove any water-soluble (leachable) component which may be present, and is thus useful if a completely non-leaching composition is desired.

Example A15

Synthesis of a Quaternary Ammonium Polyurethane that is Soluble in Alcohol, but Insoluble in Water, which has Flexible Hydrophobic Units Incorporated within the Molecular Structure (SS25HL), and which has a Low Molecular Weight The method of Example A14 was substantially followed; however, a 3:1 molar ratio of Ethoquad to 1,6-hexanediol was utilized. In addition, a less than equimolar amount of TDI was used (~65%) in order to promote the formation of short chains with hydroxyl end groups. The material is thus expected to have a lower molecular weight, and contain a relatively higher proportion of leachable (water-soluble) antimicrobial components. The exact molecular weight of the polymer is unknown; however, comparison of the viscosity of solutions of this polymer and those described above indicate that this polymer has a lower molecular weight.

Example A16

Comparison of the Quick-Action Antimicrobial Efficacy of Various Compositions Described Herein The compositions described in Examples A6, A14, and A15 were tested for quick-acting (5 minute) antimicrobial efficacy using the following procedure:

Solutions of the polymers were prepared (10% in alcohol). 50 microliters of each solution was pipetted into individual wells of plastic 24-well cell culture plates. The plates were swirled under a hand-held blowdryer to facilitate evaporation of the alcohol. Working solutions of bacteria were prepared using standard methods. Two-hundred-fifty microliters of bacterial solution ($10^4$ cfu/mL) were added to each coated well. The 24-well culture plates were incubated/shaken (37° C./100 rpm) for a desired time interval (5 min, 15 min, 30 min, or 60 min), and then 250 µL of Letheen broth (neutralizer solution) was added. The solution was removed from the wells and 100 µL was plated onto TSA and spread using standard spread plating technique, or used to make serial dilutions and then plated. Plates were incubated at 37° C. overnight, colonies were then enumerated, and antimicrobial efficacy was calculated. Testing was performed against *Staph. aureus* and *Serratia marcescens*. The relative antimicrobial efficacy of the three polymers was determined to be A15 (SS25HL)>A14 (SS50H)>A6(H3C). Sample A15 exhibited a full-kill of SA and SM after only 5 minutes. Sample A14 exhibited a full kill of SA after only 5 minutes. Sample A6 showed a full kill of SA after 30 minutes.

Example A17

Preparation of a Suture Material Coated with an Antimicrobial Composition

The polymer prepared by the method of Example A6 was used to coat multifilament polyester sutures material (Mersilene (uncoated) and Ethibond Excel (polybutylate coated), both produced and sold by Ethicon. Sutures (~10 cm length each) were washed in 70% isopropanol for 5 minutes followed by three rinses in deionized water to remove surface contamination. Sutures were allowed to dry fully before the application of the antimicrobial polymer. Samples were placed in the 50 ml conical centrifuge tubes and fully covered with the 20 ml of the appropriate treatment solution (polymer of Example A6 dissolved in isopropanol at a concentration of either 0.5, 2.0 or 10 weight %). Tubes were sonicated for 3-5 minutes in order to remove air trapped on the highly hydrophilic polyester fibers. The samples were removed from the treatment solution and allow to dry at 60-80° C. The coating process was repeated two times to assure the even coverage (three coats total). Sutures were tested against clinically relevant bacteria: *S. aureus*, SA (ATCC 6538); *E. coli* EC (ATCC 15597); *Pseudomonas aeruginosa*, PA (ATCC 15442); and Methicillin-resistant *Staphylococcus aureus*, MRSA (ATCC 33593). Bacterial suspensions were prepared according to standard methods. The concentrations of bacteria in the suspensions were measured by spectrophotometer (Milton Roy Spectronic 20D Spectrophotometer) at 580 nm for all bacteria. The measurements for *S. aureus* yield ~$10^8$ titer. The concentration of the bacteria in the stock solution was adjusted to provide a standard inoculum for experimental studies ($1 \times 10^6$ cfu/mL) with PBS. The final concentrations also were confirmed by the Colony Forming Unit (cfu) Method. The treated and control suture samples were cut aseptically into 4-5 cm lengths and stored at room temperature until use. Individual sterilized suture segments were placed in isolated wells of the sterile large-well culture plate, and exposed to the 4 mL of bacterial suspension for 3 hours. The standardized inoculate was verified by serial plate count. Sutures were freely floating in the incubation media while agitated with a shaker at 120 rpm for the duration of incubation step. After exposure to test strains, suture segments were gently washed (three times [3×]) in PBS to remove nonadherent cells. Then, the suture segments were placed in the PBS containing 0.25% of Triton-X, vortexed three times [3×], and sonicated in same solution at 20 kHz for 2-5 minutes. The suture sonicate was serially diluted in PBS before plating, and incubated for 24 hours at 37° C. Three suture segments were evaluated per inoculum challenge. Microbial recovery was expressed as log 10 cfu/cm suture segment. The following results were obtained [log reduction is in comparison to as-received (uncoated) suture material].

TABLE 1

| Treatment | Organism | Avg LR |
|---|---|---|
| 10% | SA | 5.99 (full kill) |
| 2% | SA | 5.99 (full kill) |
| 0.5% | SA | 1.34 |
| 2% | EC | 0.14 |
| 2% | PA | 1.52 |
| 10% | MRSA | 2.68 |
| 2% | MRSA | 1.37 |
| 0.5% | MRSA | 2.42 |

Example A18

Preparation of Plastic Films Coated with an Antimicrobial Composition by UV Curing The polymer described in Example A6 was blended with a UV-curable coating composition, and the mixture was used to prepare coatings on various plastic substrates. Subsequent testing using the "Agar Slurry Method" (ASTM E 2180-01) determined that the coatings had significant antimicrobial activity against various bacterial organisms, including staph aureus and E. coli, when the content of antimicrobial polymer in the coatings was between 10 and 30% by weight of the dry coating.

Example A19

Preparation of a Hydrophilic Polyurethane Foam with Antimicrobial Properties

This example demonstrates the incorporation of the alcohol-soluble/water-insoluble antimicrobial polymer described by Example A6 into a formulation used to prepare a non-leaching antimicrobial hydrophilic polyurethane foam useful as a wound dressing material. An "aqueous solution" was prepared by dissolving 90 mg of tetrasodium EDTA in 12 grams of water, then adding 10 grams of a 0.25% solution of Pluronic F-88 surfactant (BASF), and then 3 grams of ZnO 50% suspension with nonionic dispersant ("NanoShield" ZN-3010, Alfa-Aesar), followed by thorough mixing. Twenty-five grams of Hypol-2000 (Dow) was thoroughly mixed with 4 grams of a 40% solution of the polymer described in Example 6 in isopropanol, for approximately one minute. The "aqueous solution" was then added to this mixture, and thoroughly stirred with a steel spatula for between approximately 20 and 30 seconds, until uniformly mixed, and evidence of foaming was observed. The mixture was then poured onto a sheet of silicone release paper and quickly covered by a second sheet of silicone release paper held above the surface of the first paper by a spacer of desired thickness (approximately 1/16" to 1/4"). A straight-edge spreader bar was then moved across the top surface of the second sheet of paper in order to spread the mixture to a uniform thickness in-between the two sheets of release paper. The material was allowed to cure at room temperature for several minutes. The top sheet of release paper was then removed. The resulting foam, still attached to the bottom release paper, was then placed into a drying oven at 110° C. for 15 minutes. The resulting yellow foam could then be removed from the release paper for use or testing.

The cured foam was observed to quickly (<5 seconds) absorb droplets of water placed onto its surface. The absorbent capacity (drip free) of the foam was determined to be approximately 15.9 times its own weight of 1% saline solution, after immersion for 5 minutes.

The foam was tested according to ATCC Method #100, and found to give a 5.99 log reduction of Candida albicans, a 7.81-log reduction of Staph. aureus, and a 6.36-log reduction of Pseudomonas auerginosa, when compared to a non-antimicrobial hydrophilic PU foam wound dressing (Tielle, a product of J&J). The non-leaching character of the foam antimicrobial activity was demonstrated by testing extracts of the foam (24 hours @ 37° C., 60 sq-cm of foam per 20 mL of PBS) by placing 20 microliter droplets of the extracts onto marked areas of agar plates which had been spread-plated with $10^6$ cfu/mL Staph. aureus bacteria. After overnight incubation at 37° C., and subsequent visual observation, no evidence of growth inhibition was observed in the marked areas.

Example A20

Synthesis of a Quaternary Ammonium Polyurethane that is Soluble in Alcohol, but Insoluble in Water, and which has Flexible Hydrophobic and/or Hydrophilic Units Incorporated within the Molecular Structure The procedure described in Example A14 is followed, except that diethylene glycol (bis-(2-hydroxyethyl)ether) is substituted for all or part of the 1,6-hexanediol. The polymeric product will be more hydrophilic when the relative content of diethylene glycol is higher.

Example A21

Preparation of a Clear, Gel-Based Antimicrobial (SSG2) with Prolonged Durable Efficacy, for Disinfection of Skin, which Also Contains a Leachable Antimicrobial (CHG), and a Stabilizer/Preservative (EDTA)

The following ingredients were combined and mixed well to produce 100 grams of the described formulation: Ten grams of a 20% aqueous solution of CHG (chlorhexidine digluconate, Aldrich), 1.0 grams of tetrasodium EDTA dissolved in 4.0 grams of water, 25 grams of a 40% solution of SS-1C (Example 6) in isopropanol, and 60 grams of a 2% solution of PEG [poly(ethylene oxide), (MW=600,000), Aldrich] dissolved in 70/30 (volume %) isopropanol/water. The PEG was used to provide a viscous gel consistency to the formulation. The EDTA is added as a stabilizer, and/or preservative, and/or for enhanced antimicrobial efficacy. The described composition was tested on human volunteers using ASTM E 1874-97 "Standard Test Method for evaluation of Antibacterial Washes by Cup Scrub Technique". The test organism was Serratia marcescens, and a "full kill" was obtained, with an average reduction in bacterial load of greater than 3.5 logs, when compared to a non-durable control antiseptic composition (Purell Hand Sanitizer). Results were similar when antimicrobial efficacy was tested approximately five minutes after application of the formulation to the skin, and when tested four hours after application to the skin. Additionally, significant antimicrobial activity was again detected even after rinsing the treated skin with soap and water, or with alcohol.

Example A22

Preparation of a Medical Adhesive with Antimicrobial Properties

The polymer described in Example A14 was blended with low-Tg acrylate copolymers to give a composition suitable for use as a medical adhesive. The mixture was used to prepare coatings on plastic substrates. These coatings were found to have useful adhesive properties. Subsequent testing using the "Agar Slurry Method" (ASTM E 2180-01) determined that the coatings had significant antimicrobial activity against various bacterial organisms, including *staph aureus* and *E. coli*, when the content of antimicrobial polymer in the coatings was between 10 and 30% by weight of the dry coating.

Example A23

Formulation of an Antimicrobial Barrier Film for Application to Human Skin, which has Flexible Hydrophobic Units Incorporated within the Molecular Structure, and which has a Low Molecular Weight (Solution "G11")

The method of Example A14 was substantially followed; however, a ratio of 20 grams Ethoquad solution (75 wt %) to 7.5 grams of 1,6-hexanediol was utilized. In addition, a less than equimolar amount of TDI was used (~65%) in order to promote the formation of short chains with hydroxyl end groups. The material is thus expected to have a lower molecular weight, and contain a relatively higher proportion of leachable (water-soluble) antimicrobial components. The exact molecular weight of the polymer is unknown; however, comparison of the viscosity of solutions of this polymer and those described above indicated that this polymer has a lower molecular weight. The resulting polymer was formulated into a solution with the following composition:
Antimicrobial polymer (10% by weight); PEG 600K thickener (1%); Water (12%); Isopropanol (27%); and Ethanol (50%). This formulation is referred to as G-11 in the following discussion.

The cup scrub method was used to test antimicrobial efficacy of G-11 against *Serratia marcescens* on the skin of human volunteers according to ASTM E 1874-97, "*Standard Test Method for Evaluation of Antibacterial Washes by Cup Scrub Technique*". Additional experiments employing a rinsing step were also performed. The results show high antibacterial efficacy for G-11, even after rinsing the dried film with water, and are presented in the table below.

| Drying time of sanitizer on human skin (ATCC #13880) | Kill levels for *Serratia marcescens* |
|---|---|
| T = 0 | >99.98%* |
| T = 4 hours | >99.99999%* |
| T = 6 hours | >99.99999%* |

| Rinsing Study: | Efficacy after 0 rinses | Efficacy after 1 rinse** |
|---|---|---|
| G-11 (subject #1) | >99.9987%* | >99.9987%* |
| G-11 (subject #2) | >99.973% | >99.72% |
| G-11 (subject #3) | >99.9993%* | >99.9993%* |

*indicates full kill
**Rinsing step was 20 pumps (~1 ml each) of deionized water applied from standard spray bottle.

Formulation G-11 was evaluated for efficacy against the fungal organism, *Candida albicans* as follows:

Evaluation of G11 vs. *Candida albicans* by Lawn Spread

Formulation G11 was evaluated against *Candida albicans* by lawn spread technique. Cultures of *C. albicans* ATCC# MYA-905, and ATCC#10231, were grown from glycerol stocks in yeast medium broth for forty-eight hours. The cultures were then diluted to a $10^{-2}$ dilution to serve as a working inoculum. A sterile cotton swab was saturated in the inoculum and evenly spread across the entire surface of yeast medium agar. Three 30 µL quantities of G11 were then pipetted onto the agar, evenly spaced. The agar plates were moved into an incubator for forty-eight hours and then assessed for results.

Results showed that G11 prevented the growth of both strains of *C. albicans* in areas of application to the lawn spread.

Evaluation of *Candida albicans* by Glass-Slide Carrier Test

Two strains of *C. albicans*, ATCC# MYA-905, and ATCC#10231, were grown from glycerol stocks in yeast medium broth for forty-eight hours. The cultures were then diluted to a $10^{-2}$ dilution to serve as a working inoculum. 250 µL of G11 was distributed onto each of the glass slide carriers. After application the slides were placed in a biological safety cabinet for a ten minute drying period. 100 µL of *C. albicans* inoculum was added to each of the slides and gently distributed with a sterile loop, followed by a 5 minute contact time. Three treated slides and three negative control slides were used for each strain of the organism.

All slides were recovered into neutralizing solution and enumeration of G11 vs. negative control slides was accomplished by standard serial dilutions and plating.

Results showed an average log reduction of 0.78 for strain MYA-905, and a 1.71 average log reduction for strain 10231.

Antiviral efficacy analysis on the G11 skin sanitizer sample was conducted by an independent laboratory (BCS Laboratories, Inc., Gainesville, Fla.). The analysis was conducted using bacteriophage MS-2 as a model for human viruses. Bacteriophage MS-2 has been used extensively in many published research studies as a model for the inactivation of human viruses for evaluation of the potential antiviral properties of physical and chemical disinfectants in the water and healthcare industry. Its inactivation/survival correlates well with many human viruses. The antiviral efficacy testing was conducted of G11 was conducted using the well-plate model. Briefly, bacteriophage MS-2 (ATCC 15597B1; 30 nm RNA virus specific for *Escherichia coli* C3000; ATCC 15597) was used as surrogate model for human viruses. Bacteriophage stock solutions containing approximately $10^9$ plaque forming units (pfu)/mL were assayed prior to the day of challenge as per standard methods (Snustad and Dean, 1971). MS-2 stock solution was diluted to approximately $10^6$ pfu/ml in Phosphate Buffered Saline (PBS; Fisher Scientific). This phage dilution was used to evaluate the anti-bacteriophage efficacy of the Skin Sanitizer Formulation. Experimental analysis was conducted in triplicates. Analyses were conducted in 24-well cell culture plates (Corning Inc., NY).

One hundred milliliters of tested solution was pipetted into each well plate. At various time points, 100 µl of the MS-2 solution was added to the well containing the G11. The times selected for the evaluation were determined by drying time of the G11 covered surface; namely, t=0 (immediately following the addition of G11), t=30 minutes of drying, and t=4 hours of drying. Depending on the time point following the addition of the G11, the well surface was either wet (t=0 minutes) with the sanitizer or a dry invisible film was present on the surface (t=30 minutes and t=4 hours). When the wells were wet (time=0), the solutions in the well were mixed physically by repeated pipetting.

The phage and sanitizer were allowed to contact each other for either 10 seconds or 5 minutes to collect data for immediate (less than 30 seconds) and quick-acting (5 minute) antiviral efficacy.

Following the allowed contact time, 2 ml of Difco Neutralizing Buffer (Becton Dickinson, MD) was added to each well to neutralize the sanitizer and recover the MS-2 bacteriophage. Initial testing showed that this was adequate to neutralize the disinfectant present in the sanitizer. For t=30 minutes and t=4 hours the added bacteriophage was allowed to either contact the surface for 10 second or 5 minutes. For the 5 minute contact, the plate was placed on an orbital shaker (Hoefer, Red Rotor, San Francisco) on low speed for 5 minutes. Following the specified contact time, Neutralizing buffer was added to each well plate. Control (initial) bacteriophage titers were determined by adding 100 µl of bacteriophage solution to empty wells and 2 ml of Neutralizing Buffer was then added. Following the addition of Neutralizing Buffer in all the above instances, it was repeatedly pipetted and then transferred to a sterile 15 ml tube. Dilutions of solutions containing the bacteriophage were performed in PBS prior to enumeration. The number of MS-2 bacteriophage in each of the samples was enumerated as Plaque Forming Units (pfu) by an agar plaque assay using the host *E. coli* C3000 and molten Tryptic Soy Agar (TSA; Becton Dickinson, MD). Plates were allowed to incubate overnight at 37° C. and the plaques were then counted, and percent reductions as compared to the controls were determined. Each analysis was plated in duplicates. The results of repeated experiments were comparable and efficacy was reproduced in each of the time points. Results are presented in the table below, and represent the average numbers obtained from triplicate analyses.

TABLE 2

Efficacy of G11 Skin Sanitizer on the inactivation of MS-2 at various time points following the initial application at short (10 seconds) and extended (5 minutes) contact times.

| Experiment and Experimental conditions | Average MS2 pfu/ml* | Inactivation efficacy against MS-2 |
| --- | --- | --- |
| Drying time 0 minutes; 10 second contact time | $5.8 \times 10^2$ | 99.84% Inactivation |
| Drying time 0 minutes; 5 minute contact time | $2.4 \times 10^2$ | 99.93% Inactivation |
| Drying time: 30 minutes; 10 second contact time | $1.3 \times 10^6$ | Negligible (no inactivation observed) |
| Drying time: 30 minutes; 5 minute contact time | $7.8 \times 10^2$ | 99.78% Inactivation |
| Drying time: 4 hours; 10 second contact time | $1.7 \times 10^5$ | Negligible (no inactivation observed) |
| Drying time: 4 hours; 5 minute contact time | $1.1 \times 10^2$ | 99.72% inactivation |
| Recovered Initial Load (Untreated Control) | $3.5 \times 10^5$ pfu/ml* | N/A |

*pfu/ml = Plaque forming units of MS-2 in the Neutralizing Buffer recovered from each well.

Example A24

Preparation of a Solution of Water-Insoluble Antimicrobial Propylene Glycol as Solvent The polymer described in Example A14 was dried at 50° C. under vacuum to remove the alcohol solvent, and subsequently redissolved in propylene glycol to give a 40% solution of polymer in propylene glycol. This solution was observed to be clear and stable when stored at room temperature.

Example A25

Preparation of an Antimicrobial Barrier Film for Application to Human Skin, which has Improved Physical and Aesthetic Properties The composition of Example A23, while effective for antimicrobial purposes, was perceived by human volunteers to be "sticky", "gooey", "lumpy", or "stringy" either during or after application of the solution to the skin. It was determined that these undesirable physical and/or aesthetic effects were caused primarily by the thickening agent used in that formulation (1% PEG 600K). The thickening agent is used to promote high viscosity, which in turn prevents "runoff" of the product during application. It is generally desirable to use the least amount of thickening agent possible that still provides the desired level of thickening effect. Additionally, the thickening agent must be compatible with the other components of the formulation, including the alcohol solvent, and the quaternary antimicrobial polymer. Carbomer (a poly acrylate) is a common thickening agent used in skin preparations; however, it is incompatible with quaternary ammonium polymers (precipitate formation). We have discovered that using hydroxyethyl cellulose (HEC) as a thickening agent can give a compatible formulation with good viscosity properties and which lacks any undesirable physical or aesthetic effects. The grade of HEC is chosen to optimize the desired physical properties. Cellulose ethers such as methylcellulose or Methocel (Dow) are also a suitable thickening agent for the practice of this invention. The order of addition of ingredients is important in order to obtain a useful formulation.

A formulation was prepared according to the following procedure: A solution of 1.07 grams of Hydroxyethyl Cellulose ("HEC") (Cellosize #QP-100M-H, Dow) in 50 mL of water was prepared by dispersing the HEC in the water, and then swirling on a rotary mixer atr 70° C. for two hours. The solution was stored overnight, and appeared to have a smoother consistency after storage. A total of 10 g (126.5 mL) of absolute ethanol was then added to the HEC solution, followed by thorough mixing. Hence, a solution comprising approximately 0.65 wt % HEC and 70% ethanol was formed. This solution (105 grams) was mixed with 10 grams of absolute ethanol and 15 grams of a 40% solution of antimicrobial quaternary ammonium polymer in ethanol to give an antimicrobial barrier film formulation for application to skin. The antimicrobial quaternary ammonium polymer used was substantially similar to that described in Example A14. Application of this formulation to human skin, followed by rubbing-in with fingertips produced no undesirable effects. The formulation dried nicely and was not sticky while, or after, drying.

Example A26

Preparation of a Free-Standing Polymer Film Containing an Alcohol-Soluble Antimicrobial Polymer and a Plasticizer A solution was prepared by mixing 25 parts of poly(vinyl chloride) (MW=47,000; Aldrich Chemical Co, catalog # 389323), 0.3 parts Citroflex B-6 plasticizer (Moreflex, Inc), 3.3 parts of a solution of 25 weight % antimicrobial quaternary ammonium polymer dissolved in tetrahydrofuran (THF), and 20 parts of tetrahydrofuran (THF) until the components were completely dissolved and the mixture was uniform. The antimicrobial quaternary ammonium polymer used was substantially similar to that described in Example A14. The solution was poured onto a flat non-stick frying pan, and allowed to dry overnight. The frying pan was placed on a leveled surface in order to promote uniform film thickness. The dried film was peeled-away from the pan. A control film was prepared in a similar manner; however, it did not contain the antimicrobial polymer. Films were tested for antimicrobial efficacy using the ASTM "shaker flask method" (ASTM E2149—Antimicrobial Surface Test, "Determining the Antimicrobial Activity of Immobilized Antimicrobial Agents Under Dynamic Contact Conditions"). The test organism was MRSA (ATCC# BAA-44), and the contact time was 30 minutes. The film with antimicrobial content showed a 5.4 log reduction of bacteria (full kill), relative to the untreated film. Both films were similar in appearance and physical properties.

Example A27

Infusion of a Polyurethane Pellet with a Solution of Antimicrobial Polymer

A solution was prepared containing 10 grams of an antimicrobial quaternary ammonium polymer substantially similar to that described in example A15, dissolved in a mixture of 350 mL of THF and 50 mL of ethanol. To this solution was added 100 grams of polyurethane resin in the form of pellets approximately 3 mm in diameter and 3 mm long. The suspension was mixed overnight on a rotary mixer. The pellets absorbed all of the solution during this time. The pellets were dried under reduced pressure with slight heating. The dried pellets were substantially similar in appearance to the untreated pellets, with the exception that the treated pellets had a slight yellow color. No visual evidence of residual antimicrobial polymer or a coating was apparent. The pellets were tested for antimicrobial efficacy using the ASTM "shaker flask method" (ASTM E2149—Antimicrobial Surface Test, "Determining the Antimicrobial Activity of Immobilized Antimicrobial Agents Under Dynamic Contact Conditions"). The test organism was MRSA (ATCC# BAA-44), and the contact time was 30 minutes. The pellets with antimicrobial content showed a 2.5 log reduction of bacteria, relative to the untreated pellets.

Example A28

Treatment of a Substrate with a Solution of Antimicrobial Polymer

A substrate, for instance a thermoplastic polymer film comprising, for example, poly(vinyl chloride), polycarbonate, polyacrylate, or polystyrene is treated with a solution of a water-insoluble quaternary ammonium antimicrobial polymer dissolved in a suitable solvent; wherein, the suitable solvent and/or the polymer solution is capable of either dissolving (wholly or partially) absorbing-into, or otherwise penetrating the surface of the substrate. Said substrate may be treated with said solution by any suitable means, including for example, brushing, spraying, or dipping. After said treatment, the treated substrate may be dried to remove said suitable solvent, leaving said water-insoluble quaternary ammonium antimicrobial polymer infused, coated, adhered, attached, or interpenetrated to the substrate, rendering the substrate with antimicrobial properties.

Thin Film Efficacy Test (TFET):

Summary: The Thin Film Efficacy Test (TFET) was developed, based on [Bhende, S; Rothenburger, S; Spangler, D. J; In Vitro Assessment of Microbial Barrier Properties of Dermabond Topical Skin Adhesive. Surgical Infections 3(3), pp 251-257 (2002)] to determine the bacteriostatic ability of an antibacterial solution. The procedural steps of the TFET consist of applying an antibacterial solution to appropriate growth media plates and allowing the solution to completely dry. The plates are then inoculated with ~1×10$^{-6}$ CFU/ml of desired organism and subsequently incubated overnight after inoculum has completely absorbed. The area of application is then checked for bacteriostatic activity.

Plates: The media plates used for this assay are selective media plates that are appropriate to the respective organisms. Sixty plates are used for each organism.

MSA: MSA (Mannitol Salt Agar) is the selective media for *S. aureus* and MRSA.

EMB: Eosin Methylene Blue Agar is the selective media for *E. coli*.

EA: Enterococcosel Agar is the selective media for VRE.

Coating: 100 µl of the antibacterial solution is applied to each plate and allowed to air dry for a minimum of 1 hour in the biological safety cabinet before inoculating.

Inoculating: The test organism is grown in the appropriate growth media and incubated overnight unless otherwise specified. The inoculum is made to achieve a titer of 10$^6$ CFU/ml. The coated plates are then inoculated with 1000 µl bacterial solution and the inoculum is then homogenously applied by moving the plate in a circular motion.

Exposure: The samples are incubated at 37° C. in a high humidity chamber and the exposure time is overnight unless otherwise stated.

Results: After incubation, each plate is inspected for bacteriostatic activity on the area of application. The results are read as Pass/Fail. If there is no growth, the plate is read as Pass and if there is growth on the area, the plate is read as Fail.

TFET—Results:

Example T1

The Thin Film Efficacy Test (TFET) was used to determine the bacteriostatic ability of the antimicrobial solution. The procedural steps of the TFET consist of using growth media plates as carriers in which 100 µl of the chosen antimicrobial solution is applied in the center of the plate. The antimicrobial solution was allowed to air dry for a minimum of 1 hour prior to inoculation. The coated plates were inoculated with 1000 µl inoculum at a titer of 10$^6$ CFU/ml. The inoculum was homogeneously applied by swirling the plate until the inoculum completely covered the entire surface area of the plate. The inoculated plates were then allowed to dry and subsequently incubated overnight at 37° C. Following overnight incubation, the area of antimicrobial solution application was checked for suppression of bacterial growth and the results were read as Pass/Fail. If suppression of growth was observed, the plate was considered passing. If no suppression of growth as observed, the plate was considered failing. The media used for *S. aureus*, ATCC #6538, was Mannitol Salt Agar (MSA) and the antimicrobial solution used was H3-C (From Example A6).

The results for *S. aureus* were as follows:

| Antimicrobial Solution | 24 hr Results | 48 hr Results |
|---|---|---|
| 5% H3-C | 60 Pass/0 Fail | 60 Pass/0 Fail |
| 10% H3-C | 60 Pass/0 Fail | 60 Pass/0 Fail |

Example T2

Example T2 uses Methicillin-Resistant *S. aureus* (MRSA, ATCC #BAA-44) as the test organism and again MSA is used as the growth media.
The results for MRSA are as follows:

| Antimicrobial Solution | 24 hr Results | 48 hr Results |
|---|---|---|
| 5% H3-C | 60 Pass/0 Fail | 60 Pass/0 Fail |

Example T3

Example T3 used *E. coli*, ATCC #15597, as the test organism and additionally Eosin Methylene Blue Agar was used as the growth media.
The results for *E. coli* were as follows:

| Antimicrobial Solution | 24 hr Results | 48 hr Results |
|---|---|---|
| 5% H3-C | 60 Pass/0 Fail | 60 Pass/0 Fail |
| 10% H3-C | 60 Pass/0 Fail | 60 Pass/0 Fail |

Example T4

Example T4 used Vancomycin-Resistant *Enterococcus* (VRE, ATCC #700221) as the test organism and additionally used Enterococcosel Agar as the growth media.
The results for VRE were as follows:

| Antimicrobial Solution | 24 hr Results | 48 hr Results |
|---|---|---|
| 5% H3-C | 60 Pass/0 Fail | 60 Pass/0 Fail |

Example T5

Example T5 used the H-1 formulation (see Example A3) as the antimicrobial solution.
The results for *S. aureus* were as follows:

| Antimicrobial Solution | 24 hr Results | 48 hr Results |
|---|---|---|
| 10% H-1 | 60 Pass/0 Fail | 60 Pass/0 Fail |

Example T6

Example T6 also used the H-1 formulation as the antimicrobial solution.
The results for *E. coli* were as follows:

| Antimicrobial Solution | 24 hr Results | 48 hr Results |
|---|---|---|
| 10% H-1 | 60 Pass/0 Fail | 60 Pass/0 Fail |

Comparative Example T7

For comparison with compositions of the present invention, Example T7 used Zero brand hand sanitizer (Aquagen International, Inc.) as the antimicrobial solution.
The results for *S. aureus* were as follows:

| Antimicrobial Solution | 24 hr Results | 48 hr Results |
|---|---|---|
| Zero | 8 Pass/52 Fail | 0 Pass/60 Fail |

Comparative Example T8

For comparison with compositions of the present invention, Example T8 also used Zero brand hand sanitizer as the antimicrobial solution.
The results for *E. coli* were as follows:

| Antimicrobial Solution | 24 hr Results | 48 hr Results |
|---|---|---|
| Zero | 0 Pass/60 Fail | 0 Pass/60 Fail |

Comparative Example T9

For comparison with compositions of the present invention, Example T9 used Purell brand hand sanitizer (GOJO Industries, Inc.) as the antimicrobial solution.
The results for *S. aureus* were as follows:

| Antimicrobial Solution | 24 hr Results | 48 hr Results |
|---|---|---|
| Purell | 0 Pass/60 Fail | 0 Pass/60 Fail |

Comparative Example T10

For comparison with compositions of the present invention, Example T10 also used Purell brand hand sanitizer (GOJO Industries, Inc.) as the antimicrobial solution.
The results for *E. coli* were as follows:

| Antimicrobial Solution | 24 hr Results | 48 hr Results |
|---|---|---|
| Purell | 0 Pass/60 Fail | 0 Pass/60 Fail |

Carrier Persistence Test (CPT):
Summary: This procedure is a modification of the EPA's Standard Operating Procedure: Testing of Spray Disinfectants against *Staphylococcus aureus, Pseudomonas aeruginosa*, and *Mycobacterium bovis*;

which is an adaptation of the AOAC method to determine the efficacy of spray products as hard surface disinfectants against three test organisms, *Mycobacterium bovis* (BCG), *Pseudomonas aeruginosa*, and *Staphylococcus aureus*.

The procedural steps of the CPT consist of applying an antimicrobial test solution to chosen carriers and allowing the carriers to dry before they are inoculated with the appropriate test organism. After inoculation, the carriers are incubated for the prescribed exposure time, subsequently placed into neutralizing solution, then serial diluted and plated for efficacy quantification using standard methods.

Carriers: The carriers are 25 cm² and can be comprised of a variety of materials. The carriers are sterilized by methods appropriate to the carrier's composition. The three carriers types used in these assays are borosilicate glass, Vitro-Skin, and pig skin; however, carriers suitable for use in this method are not limited to the aforementioned.

Borosilicate
Glass: Borosilicate glass slides are washed with ethanol and allowed to air dry. After drying, the borosilicate glass slides are placed into Petri dishes and autoclaved for 15 minutes.

Vitro-Skin: The Vitro-Skin is prepared according to manufacturer's specifications. If Vitro-Skin becomes unsterile, it needs to be sterilized with 70% alcohol, allowed to dry, and re-hydrated according to the manufacturer's specifications. Vitro-Skin was directly purchased from the manufacturer (IMS Inc., Orange, Conn.). VITRO-SKIN is an advanced testing substrate that effectively mimics the surface properties of human skin. It contains both optimized protein and lipid components and is designed to have topography, pH, critical surface tension and ionic strength similar to human skin.

Pig Skin: The pig skin is sterilized with 70% alcohol. This procedure includes thoroughly wetting the carriers with the 70% alcohol and allowing the carriers to thoroughly air dry in a Biological Safety Cabinet (BSC). As an alternative, the pig skin may be exposed to UV light for 10 minutes. Fresh pig skin is purchased from a local slaughterhouse.

Application: The antimicrobial solution is applied to each carrier until it thoroughly wets the carriers. The solution volume should not exceed 1000 PI and will not be less than 20 µl. The antimicrobial solution is then allowed to air dry for a minimum of 1 hour in a BSC before inoculating.

Inoculation: Test organisms are grown in appropriate growth media and incubated overnight at 37° C. unless otherwise specified. The inoculum is modified to produce a titer of $10^8$ CFU/ml. The carriers carrying the antimicrobial solution is then inoculated with 10 µl-20 µl of inoculum. The inoculum will be distributed with sterile swabs saturated with inoculum. Exposure time begins directly after inoculation.

Exposure: The exposure time is overnight unless otherwise specified and samples are incubated at 37° C. in a high humidity chamber.

Neutralization: Inoculated carriers are neutralized before recovering the organisms to stop antimicrobial activity of the antimicrobial solution. All neutralizations are done with 20 ml aliquots of Letheen Broth in 50 ml conical centrifuge tubes at a minimum of 10 minutes unless otherwise specified.

Recovery: Organism recovery is started within the neutralization tubes. The neutralized carriers are vortexed for 1 minute and the organisms are subsequently recovered with standard serial dilution and plating methods. Plates are incubated overnight at 37° C. and colony forming units are quantified the following day.

Controls: Carrier substrates without any applied antimicrobial coating are used as negative controls to determine the baseline microbial growth. Control substrates were of the same composition as the test substrates within each sample set. Colony counts for the control substrates are reported.

Calculations: Calculations will be computed using a Microsoft Excel spreadsheet. Electronic copies of the spreadsheet as well as hard copies will be retained.

To calculate CFU/mL per carrier:

$$[(\text{avg. CFU for } 10^{-w}) + (\text{avg. CFU for } 10^{-x}) + (\text{avg. CFU for } 10^{-y}) + (\text{avg. CFU for } 10^{-z})]/(10^{-w} + 10^{-x} + 10^{-y} + 10^{-z})$$

where $10^{-w}$, $10^{-x}$, $10^{-y}$, and $10^{-z}$ are the dilutions plated. In the event that one or more dilutions yield plate counts greater than 300, or less than 30, those counts and their corresponding dilutions will not be used in the calculations. In the event that only one of two plates has counts yielding 300 CFU or less, that plate count and its corresponding dilution will be included but no average will be determined.

NOTE: Plate counts of 0 are to be included in all calculations.

To calculate Log Reduction:

$$LR = \text{Log}\,[(\text{CFU/ml for treated carrier})/(\text{CFU/ml for control carrier})]$$

Carrier Persistence Test

Results

Example C1

A 10% solution of H-1 antimicrobial polymer (See Example A3) was applied to borosilicate glass slide carriers. Using the tip of a pipette, 250 µl of NimbuDerm H-1 was homogenously applied over the 25 cm² surface of the glass slide carrier. The glass slide carriers were allowed to dry for at least 1 hour prior to inoculation. The carriers were inoculated with 10 µl of $10^8$ CFU/ml inoculum of to ensure a target load of $10^6$ CFU/ml. The organism used was *S. aureus* ATCC # 6538, and the allowed exposure time was 30 minutes. Following the exposure, the inoculated glass slide carriers were placed in neutralizing solution of 20 ml Letheen Broth for no less than 10 minutes to allow for proper neutralization—the Letheen broth was chilled to 4° C. prior to use. Following neutralization, the carriers were vortexed in the neutralization broth for one minute to facilitate the recovery of the organism. The recovery of viable organisms was done by standard serial dilution and plating methods.

Results were as follows:
*S. aureus* control carrier population: $3.20 \times 10^6$ CFU/ml
Carrier: Borosilicate glass slides
Exposure time: 30 min

| Samples | Solution | Log Reduction |
|---|---|---|
| 1 | 10% H-1 | 6.51* |
| 2 | 10% H-1 | 6.51* |
| 3 | 10% H-1 | 6.51* |
| 4 | 10% H-1 | 6.51* |

(*= full kill)

Example C2

Example C2 is identical to Example C1 with the exception to the exposure time. The exposure time used for Example C2 was 16 hours (overnight exposure).

Results were as follows:
*S. aureus* control carrier population: 2.30E07 CFU/ml
Carrier: Borosilicate glass slides
Exposure time: 16 hours

| Samples | Solution | Log Reduction |
| --- | --- | --- |
| 1 | 10% H-1 | 7.36* |
| 2 | 10% H-1 | 7.36* |
| 3 | 10% H-1 | 7.36* |
| 4 | 10% H-1 | 7.36* |
| 5 | 10% H-1 | 7.36* |
| 6 | 10% H-1 | 7.36* |

(* = full kill)

Example C3

Example C3 is identical to Example C2 with the exception of the organism. The organism used was *E. coli* ATCC 15597.
Results were as follows:
*E. coli* control carrier population: 1.06E05 CFU/ml
Carrier: Borosilicate glass slides
Exposure time: 16 hours

| Samples | Solution | Log Reduction |
| --- | --- | --- |
| 1 | 10% H-1 | 5.03* |
| 2 | 10% H-1 | 5.03* |
| 3 | 10% H-1 | 5.03* |
| 4 | 10% H-1 | 5.03* |
| 5 | 10% H-1 | 5.03* |
| 6 | 10% H-1 | 5.03* |

(* = full kill)

Example C4

Example C4 is identical to Example C3 with the exception of the carrier. The carrier used was Vitro-Skin.
Results were as follows:
*E. coli* control carrier population: 2.87E06 CFU/ml
Carrier: Vitro-Skin
Exposure time: 16 hours

| Samples | Solution | Log Reduction |
| --- | --- | --- |
| 1 | 10% H-1 | 6.46* |
| 2 | 10% H-1 | 6.46* |
| 3 | 10% H-1 | 6.46* |
| 4 | 10% H-1 | 6.46* |
| 5 | 10% H-1 | 6.46* |
| 6 | 10% H-1 | 6.46* |

(* = full kill)

Example C5

A 10% solution of H-3 antimicrobial polymer (see Example A6) was applied to borosilicate glass slide carriers. Using the tip of a pipette, 250 µl of H-3 (10% polymer content) was homogenously applied over the 25 cm² surface of the glass slide carrier. The glass slide carriers were allowed to dry for at least 1 hour prior to inoculation. The carriers were inoculated with 10 µl of $10^8$ CFU/ml inoculum to ensure a target load of $10^6$ CFU/ml. The organism used was *S. aureus* ATCC #6538 the allowed exposure time was 30 minutes. Following the exposure, the inoculated glass slide carriers were placed in neutralizing solution of 20 ml Letheen Broth for no less than 10 minutes to allow for proper neutralization. The Letheen broth was chilled to 4° C. prior to use. Following neutralization, the carriers were vortexed in the neutralization broth for one minute to facilitate the recovery of the organism. The recovery of viable organisms was performed by standard serial dilution and plating methods.
Results were as follows:
*E. coli* control carrier population: 1.06E05 CFU/ml
Carrier: Borosilicate glass slides
Exposure time: 16 hours

| Samples | Solution | Log Reduction |
| --- | --- | --- |
| 1 | 10% H-3 | 5.03* |
| 2 | 10% H-3 | 5.03* |
| 3 | 10% H-3 | 5.03* |
| 4 | 10% H-3 | 5.03* |
| 5 | 10% H-3 | 5.03* |
| 6 | 10% H-3 | 5.03* |

(* = full kill)

Example C6

Example C6 is identical to Example C5 with the exception of the carrier. The carrier used was Vitro-Skin.
Results were as follows:
*E. coli* control carrier population: 2.87E06 CFU/ml
Carrier: Vitro-Skin
Exposure time: 16 hours

| Samples | Solution | Log Reduction |
| --- | --- | --- |
| 1 | 10% H-3 | 6.46* |
| 2 | 10% H-3 | 6.46* |
| 3 | 10% H-3 | 6.46* |
| 4 | 10% H-3 | 6.46* |
| 5 | 10% H-3 | 6.46* |
| 6 | 10% H-3 | 6.46* |

(* = full kill)

Example C7

Example C7 is identical to Example C5 with the exception of the concentration of skin sanitizer solution. The H3-C skin sanitizer's concentration is now reduced to 7%.
Results were as follows:
*E. coli* control carrier population: 2.50E06 CFU/ml
Carrier: Borosilicate glass slides
Exposure time: 16 hours

| Samples | Solution | Log Reduction |
| --- | --- | --- |
| 1 | 7% H3-C | 6.40* |
| 2 | 7% H3-C | 6.40* |
| 3 | 7% H3-C | 6.40* |
| 4 | 7% H3-C | 6.40* |
| 5 | 7% H3-C | 6.40* |
| 6 | 7% H3-C | 6.40* |

(* = full kill)

Example C8

Example C8 is identical to Example C7 with the exception of the carrier. The carrier used was Vitro-Skin.
Results were as follows:
E. *coli* control carrier population: 2.08E06 CFU/ml
Carrier: Vitro-Skin
Exposure time: 16 hours

| Samples | Solution | Log Reduction |
|---|---|---|
| 1 | 7% H3-C | 6.32* |
| 2 | 7% H3-C | 6.32* |
| 3 | 7% H3-C | 6.32* |
| 4 | 7% H3-C | 6.32* |
| 5 | 7% H3-C | 6.32* |
| 6 | 7% H3-C | 6.32* |

(*= full kill)

Example C9

Example C9 is identical to Example C7 with the exception of the concentration of skin sanitizer solution. The H3-C skin sanitizer's concentration is now further reduced to 1%.
Results were as follows:
E. *coli* control carrier population: 2.77E04 CFU/ml
Carrier: Borosilicate glass slides
Exposure time: 16 hours

| Samples | Solution | Log Reduction |
|---|---|---|
| 1 | 1% H3-C | 4.44* |
| 2 | 1% H3-C | 4.44* |
| 3 | 1% H3-C | 4.44* |
| 4 | 1% H3-C | 4.44* |
| 5 | 1% H3-C | 4.44* |
| 6 | 1% H3-C | 4.44* |

(*= full kill)

Example C10

Example C10 is identical to Example C9 with the exception of the organism. The organism used was *S. aureus* ATCC # 6538.
Results were as follows:
*S. aureus* control carrier population: 1.25E03 CFU/ml
Carrier: Borosilicate glass slides
Exposure time: 16 hours

| Samples | Solution | Log Reduction |
|---|---|---|
| 1 | 1% H3-C | 3.10* |
| 2 | 1% H3-C | 3.10* |
| 3 | 1% H3-C | 3.10* |
| 4 | 1% H3-C | 3.10* |
| 5 | 1% H3-C | 3.10* |
| 6 | 1% H3-C | 3.10* |

Example C11

Example C11 is identical to Example C10 with the exception of the organism. The organism used was *P. aeruginosa* ATCC #15442.
Results were as follows:
*P. aeruginosa* control carrier population: 3.93E06 CFU/ml
Carrier: Borosilicate glass slides
Exposure time: 16 hours

| Samples | Solution | Log Reduction |
|---|---|---|
| 1 | 1% H3-C | 6.59* |
| 2 | 1% H3-C | 6.59* |
| 3 | 1% H3-C | 6.59* |
| 4 | 1% H3-C | 6.59* |
| 5 | 1% H3-C | 6.59* |
| 6 | 1% H3-C | 6.59* |

(*= full kill)

Example C12

A 1% solution H3-C antimicrobial polymer was applied to borosilicate glass slide carriers. The sanitizer solution was applied by passing over the 25 cm² slide surface two times using a nonwoven wipe material (polyester/cotton) saturated with sanitizer solution. The now coated glass slide carriers were allowed to dry for at least 1 hour prior to inoculation. The coated glass slides were then inoculated with an inoculum of $10^8$ CFU/ml to ensure a target load of $10^6$ CFU/ml. The organism used was *E. coli* ATCC 15597 and the allowed exposure time was 16 hours. Following the exposure, the inoculated glass slide carriers were placed into a neutralizing solution of 20 ml Letheen Broth for no less than 10 minutes to allow for proper neutralization. The Letheen broth was chilled to 4° C. prior to use. Following neutralization, the carriers were vortexed in the neutralization broth for one minute to facilitate the recovery of the organism. The recovery of viable organisms was performed by standard serial dilution and plating methods.
Results were as follows:
*E. coli* control carrier population: 1.57E06 CFU/ml
Carrier: Borosilicate glass slides
Exposure time: 16 hours

| Samples | Solution | Log Reduction |
|---|---|---|
| 1 | 1% H3-C | 6.19* |
| 2 | 1% H3-C | 6.19* |
| 3 | 1% H3-C | 6.19* |
| 4 | 1% H3-C | 6.19* |
| 5 | 1% H3-C | 6.19* |
| 6 | 1% H3-C | 6.19* |

(*= full kill)

Example C13

Example C13 is identical to Example C12 with the exception of the organism. The organism used was *P. aeruginosa* ATCC #15442.
Results were as follows:
*P. aeruginosa* control carrier population: 4.70E06 CFU/ml
Carrier: Borosilicate glass slides
Exposure time: 16 hours

| Samples | Solution | Log Reduction |
|---|---|---|
| 1 | 1% H3-C | 6.67* |
| 2 | 1% H3-C | 6.67* |
| 3 | 1% H3-C | 6.67* |
| 4 | 1% H3-C | 6.67* |
| 5 | 1% H3-C | 6.67* |
| 6 | 1% H3-C | 6.67* |

(*= full kill)

Comparative Example C14

Purell brand instant hand sanitizer solution (GOJO Industries, Inc.) was applied to borosilicate glass slide carriers. Using the tip of a pipette, 250 uL of Purell was homogenously applied over the 25 cm² surface of the glass slide carrier. The glass slide carriers were allowed to dry for at least 1 hour prior to inoculation. The carriers were inoculated with 10 uL of $10^8$ CFU/ml inoculum to ensure a target load of $10^6$ CFU/ml. The organism used was S. aureus ATCC #6538, and the allowed exposure time was 30 minutes. Following the exposure, the inoculated glass slide carriers were placed in neutralizing solution of 20 ml Letheen Broth for no less than 10 minutes to allow for proper neutralization. The Letheen broth was chilled to 4° C. prior to use. Following neutralization, the carriers were vortexed in the neutralization broth for one minute to facilitate the recovery of the organism. The recovery of viable organisms was performed by standard serial dilution and plating methods.
Results were as follows:
S. aureus control carrier population: 1.02E05 CFU/ml
Carrier: Borosilicate glass slides
Exposure time: 30 minutes

| Samples | Solution | Log Reduction |
|---|---|---|
| 1 | Purell | 1.07 |
| 2 | Purell | 1.22 |
| 3 | Purell | 1.17 |
| 4 | Purell | 1.07 |
| 5 | Purell | 1.19 |
| 6 | Purell | 1.14 |

Comparative Example C15

Example C15 is identical to Example C14 with the exception of the organism. The organism used was E. coli ATCC # 15597.
Results were as follows:
E. coli control carrier population: 4.70E06 CFU/ml
Carrier: Borosilicate glass slides
Exposure time: 30 min

| Samples | Solution | Log Reduction |
|---|---|---|
| 1 | Purell | 0.89 |
| 2 | Purell | 0.50 |
| 3 | Purell | −1.46 |
| 4 | Purell | −4.95 |
| 5 | Purell | 0.75 |

Comparative Example C16

Example C16 is identical to Example C14 with the exception of the organism. The organism used was P. aeruginosa ATCC #15442.
Results were as follows:
P. aeruginosa control carrier population: 4.70E06 CFU/ml
Carrier: Borosilicate glass slides
Exposure time: 30 min

| Samples | Solution | Log Reduction |
|---|---|---|
| 1 | Purell | 0.37 |
| 2 | Purell | 0.33 |
| 3 | Purell | 0.37 |

Example C17

The material of Example A9 (SS-1C) was applied to pig skin carriers. Using the tip of a pipette, 1000 μl of SS-1C was homogenously applied over the 25 cm² surface of the pig skin carrier. The pig skin carriers were allowed to dry for at least 1 hour prior to inoculation. The carriers were inoculated with 20 μl of $10^8$ CFU/ml inoculum of to ensure a target load of $10^6$ CFU/ml. The organism used was Serratia. marcescens, ATCC #13380. The allowed exposure time was 4 hours. Following the exposure, the inoculated pig skin carriers were placed in neutralizing solution of 20 ml Letheen Broth for no less than 10 minutes to allow for proper neutralization—the Letheen broth was chilled to 4° C. prior to use. Following neutralization, the carriers were vortexed in the neutralization broth for one minute to facilitate the recovery of the organism. The recovery of viable organisms was done by standard serial dilution and plating methods.
Results were as follows:
S. marcescens control carrier population: 1.18E07 CFU/ml
Carrier: Pig Skin
Exposure time: 4 hours

| Samples | Solution | Log Reduction |
|---|---|---|
| 1 | 10% SS-C | 7.07 |
| 2 | 10% SS-C | 7.07 |
| 3 | 10% SS-C | 7.07 |

Example C18

Example C18 is identical to Example C17 with the exception of the organism. The organism used was E. coli ATCC 8739.
Results were as follows:
E. coli control carrier population: 1.54E07 CFU/ml
Carrier: Pig Skin
Exposure time: 4 hours

| Samples | Samples | Log Reduction |
|---|---|---|
| 1 | 10% SS-C | 7.19 |
| 2 | 10% SS-C | 7.19 |
| 3 | 10% SS-C | 7.19 |

Example C19

Example C19 is identical to Example C17 with the exception of the organism. The organism used was MRSA (Methacillin-resistant *Staph. aureus*)
Results were as follows:
MRSA control carrier population: 2.63E07 CFU/ml
Carrier: Pig Skin
Exposure time: 4 hours

| Samples | Solution | Log Reduction |
|---|---|---|
| 1 | 10% SS-C | 7.42 |
| 2 | 10% SS-C | 7.42 |
| 3 | 10% SS-C | 7.42 |

Example C20

Example C20 is identical to Example C17 with the exception of the organism. The organism used was VRE, (Vancomycin resistant *Enterococus*)
Results were as follows:
VRE control carrier population: 3.23E06 CFU/ml
Carrier: Pig Skin
Exposure time: 4 hours

| Samples | Solution | Log Reduction |
|---|---|---|
| 1 | 10% SS-C | 6.51 |
| 2 | 10% SS-C | 6.51 |
| 3 | 10% SS-C | 6.51 |

Having generally described this invention, including the best mode thereof, those skilled in the art will appreciate that the present invention contemplates the embodiments of this invention as defined in the following claims, and equivalents thereof. However, those skilled in the art will appreciate that the scope of this invention should be measured by the claims appended hereto, and not merely by the specific embodiments exemplified herein. Those skilled in the art will also appreciate that more sophisticated technological advances will likely appear subsequent to the filing of this document with the Patent Office. To the extent that these later developed improvements embody the operative principles at the heart of the present disclosure, those improvements are likewise considered to come within the ambit of the following claims.

What is claimed is:

1. A method of fabricating an antimicrobial substrate consisting essentially of the steps of:
    a. preparing a composition, wherein said composition comprises (1) a solvent consisting essentially of acetone, methyl ethyl ketone, tetrahydrofuran, ethyl acetate, an ether, an ester, benzene, toluene, a carbonate, a hydrocarbon, a chlorinated hydrocarbon, an alcohol, a glycol, or a mixture thereof, and (2) an antimicrobial polymer wherein said antimicrobial polymer is (a) a polyurethane polymer or (b) a polymer comprising allyl- or vinyl-containing monomers, and
    wherein said antimicrobial polymer further comprises a monomeric moiety covalently bound to the molecular structure of the polymer, wherein said monomeric moiety has at least one quaternary ammonium group,
    wherein there is at least one mole of quaternary ammonium moieties per 650 grams of said antimicrobial polymer,
    wherein said antimicrobial polymer is readily soluble in said solvent but insoluble in water,
    wherein said solvent serves as a carrier for combining said antimicrobial polymer with a substrate, and
    wherein said antimicrobial activity is not provided by an antimicrobial metallic material,
    b. applying said composition to said substrate, wherein said composition is wholly or partially infused, absorbed-into, penetrated, impregnated, coated, adhered, attached, interpenetrated, or otherwise incorporated into or onto said substrate, and
    c. drying or evaporating said solvent, whereby said antimicrobial polymer remains on or in said substrate upon exposure to aqueous fluids, and whereby said antimicrobial polymer imparts durable antimicrobial activity to said substrate.

2. The method of claim 1, wherein said solvent consists essentially of an alcohol, a glycol, or a mixture thereof.

3. The method of claim 1, wherein said composition of step a further comprises (3) a UV-curable coating composition.

4. The method of claim 1, wherein said antimicrobial substrate is a cosmetic formulation comprising said antimicrobial polymer.

5. The method of claim 1, further comprising the step of incorporating said substrate into an article prior to step c whereby an antimicrobial article is produced, and whereby said antimicrobial polymer remains on or in said antimicrobial article upon exposure to aqueous fluids.

6. The method of claim 5, wherein said substrate comprises a polymer, textile, wood, or paper.

7. The method of claim 5, wherein said antimicrobial article is a suture or a wound dressing.

8. The method of claim 5, wherein said antimicrobial article is selected from the group consisting of a suture, a wound dressing, a film, a fiber, a gel, a foam, an adhesive, a sealant, a caulk, a tube, a sheet, a rod, a coating, and a powder.

9. The method of claim 8, wherein said antimicrobial article is a wound dressing comprising an antimicrobial foam.

10. The method of claim 8, wherein said antimicrobial article is a suture.

11. The method of claim 8, wherein said antimicrobial article is an adhesive.

12. The method of claim 8, wherein said antimicrobial article is a tube.

13. The method of claim 8, wherein said antimicrobial article is a wound dressing.

14. The method of claim 1, wherein said allyl- or vinyl-containing monomeric moiety is a vinylbenzyltrimethylammonium salt or a diallyldialkylammonium salt.

15. The method of claim 1, wherein said composition of step a further comprises at least one additive selected from the group consisting of a drug, an antimicrobial agent, an antiseptic agent, a thickening agent, a moisturizer, an emollient, a vitamin, a temporary dye, a permanent dye, and a UV absorber, whereby the antimicrobial article has additional characteristics resulting from incorporating said composition.

16. The method of claim 15, wherein said additive is a leachable antimicrobial agent selected from the group consisting of quaternary ammonium salts, biguanides, and phenolic compounds.

17. The method of claim 16, wherein said leachable antimicrobial agent is selected from the group consisting of benzalkonium chloride, benzethonium chloride, dimethyldidecyl ammonium chloride, chlorhexidine, poly(hexamethylene biguanide), phenol, triclosan and mixtures thereof.

18. The method of claim 17, wherein said additive is an emollient selected from the group consisting of glycerol, ethylene glycol, propylene glycol, butylene glycol, pentane glycol, dipropylene glycol, polypropylene glycol, polyethylene glycol, mineral oil, fatty alcohol, lanolin, silicone, isopropyl palmitate, squalane, glycerin, an isomer or derivative thereof, and a mixture of any of the aforesaid.

19. The method of claim 1, wherein at least one nitrogen of said at least one quaternary ammonium group of said monomeric moiety is in the main-chain of said antimicrobial polymer.

* * * * *